United States Patent
Kawakami et al.

(10) Patent No.: US 7,786,470 B2
(45) Date of Patent: Aug. 31, 2010

(54) SWITCHING ELEMENT

(75) Inventors: Haruo Kawakami, Tokyo (JP); Hisato Kato, Tokyo (JP); Masami Kuroda, Tokyo (JP); Nobuyuki Sekine, Tokyo (JP); Keisuke Yamashiro, Tokyo (JP)

(73) Assignee: Fuji Electric Holdings Co., Ltd. (JP)

( * ) Notice: Subject to any disclaimer, the term of this patent is extended or adjusted under 35 U.S.C. 154(b) by 1139 days.

(21) Appl. No.: 10/545,854

(22) PCT Filed: Feb. 17, 2004

(86) PCT No.: PCT/JP2004/001750

§ 371 (c)(1), (2), (4) Date: Jan. 11, 2006

(87) PCT Pub. No.: WO2004/073081

PCT Pub. Date: Aug. 26, 2004

(65) Prior Publication Data

US 2007/0063187 A1     Mar. 22, 2007

(30) Foreign Application Priority Data

Feb. 17, 2003  (JP) ............................. 2003-038530
Sep. 30, 2003  (JP) ............................. 2003-341488

(51) Int. Cl.
 *H01L 35/24* (2006.01)
(52) U.S. Cl. .......... 257/40; 257/E51.001; 257/E51.008; 438/99; 532/1
(58) Field of Classification Search .................. 257/40, 257/E51.008, E51.001; 438/82, 99, 780
See application file for complete search history.

(56) References Cited

U.S. PATENT DOCUMENTS

| 3,833,894 A | 9/1974 | Aviram et al. |
| 4,652,894 A | 3/1987 | Potember et al. |

(Continued)

FOREIGN PATENT DOCUMENTS

EP   0 109 240 A1   5/1984

(Continued)

OTHER PUBLICATIONS

Liping Ma "Organic bistable light-emitting devices" Applied Physics Letters, vol. 80, No. 3, Jan. 21, 2002 (pp. 362-364).*

(Continued)

*Primary Examiner*—Khiem D Nguyen
(74) *Attorney, Agent, or Firm*—Rossi, Kimms & McDowell LLP

(57) ABSTRACT

The present invention provides a switching element that has a stable bistable characteristic and a high transition voltage and demonstrates excellent cyclic performance. The switching element has two stable resistance values with respect to the voltage applied between electrodes, wherein a first electrode layer, an organic bistable material layer, and a second electrode layer are successively formed as thin films on a substrate and the organic bistable material constituting the organic bistable material layer is a quinomethane-based compound or a monoquinomethane-based compound. A metal constituting the second electrode layer is diffused into the organic bistable material layer. It is preferred that the second electrode layer be formed by vapor deposition and the temperature of the substrate during the vapor deposition be 30-150° C.

3 Claims, 9 Drawing Sheets

U.S. PATENT DOCUMENTS

| | | | |
|---|---|---|---|
| 5,334,856 A | | 8/1994 | Otsuka et al. |
| 5,844,363 A | * | 12/1998 | Gu et al. ............... 313/506 |
| 6,825,359 B2 | * | 11/2004 | Ohkura et al. ............ 549/78 |
| 2003/0129368 A1 | | 7/2003 | Berneth |
| 2004/0031965 A1 | * | 2/2004 | Forrest et al. ............ 257/79 |
| 2006/0102892 A1 | | 5/2006 | Kawakami et al. |

FOREIGN PATENT DOCUMENTS

| | | | |
|---|---|---|---|
| JP | 52-083594 A | | 7/1977 |
| JP | 5-80374 A | | 4/1993 |
| JP | 05080374 A | | 4/1993 |
| JP | 63-241548 A | | 10/1998 |
| JP | 2000-012922 A | | 1/2000 |
| JP | 2001-160492 A | | 6/2001 |
| JP | 3199430 B2 | | 6/2001 |
| JP | 3313405 B2 | | 5/2002 |
| JP | 2002-324683 A | | 11/2002 |
| JP | 2003-105039 A | | 4/2003 |
| JP | 2003-228185 A | | 8/2003 |
| JP | 2003-238561 A | | 8/2003 |
| WO | 02/37500 A1 | | 5/2002 |
| WO | WO 02/37500 A | | 5/2002 |
| WO | WO 02/37500 A1 | | 5/2002 |
| WO | 2004/073079 A1 | | 8/2004 |
| WO | 2004073079 A1 | | 8/2004 |

OTHER PUBLICATIONS

Mizoguchi Akira (JP Publication 05-080374) "Organic Nonlinear Optical Material" (Feb. 4, 1993) (Machine English Translation).*
Kuroda Masami "Electrophotographic Photoreceptor", Japan Pub. 2001-142239 (May 25, 2001), Machine English Translation.*
Kawakami, et al., Organic Bistable Devices with High Switching Voltage, Fuji Electric Advanced Technology Corporate Ltd., Organic Field-Effect Transistors III, pp. 9-16, Proceedings of SPIE vol. 5522, SPIE, Bellingham, WA, Oct. 2004.
Kawakami, et al., Electrical Bistable Behaviors of Organic Materials in Single Layer Structure, Fuji Electric Corporate Research & Development Ltd., Organic Field Effect Transistors II, pp. 71-79, Proceedings of SPIE vol. 5217, SPIE, Bellingham, WA, Nov. 2004.
Ma, et al., Nonvolatile Electrical Bistability of Organic/Metal-Nanocluster/Organic System, Department of Materials Science and Engineering, University of California at Los Angles, CA, pp. 1419-1421, Applied Physics Letters, vol. 82, No. 9, Mar. 2003.
Ma, et al., Organic Electrical Bistable Devices and Rewritable Memory Cells, Department of Materials Science and Engineering, University of California at Los Angles, CA, pp. 2997-2999, Applied Physics Letters, vol. 80, No. 16, Apr. 2002.
Ma, et al., Organic Bistable Light-Emitting Devices, Department of Materials Science and Engineering, University of California at Los Angles, CA, pp. 362-364, Applied Physics Letters, vol. 80, No. 3, Jan. 2002.
Relevant portion of Partial European Search Report of corresponding PCT Application EP/04711724.
Horiuchi et al, "Quantum Phase Transition in Organic Charge-Transfer Complexes," SCIENCE, Jan. 1, 2003, pp. 229-232, vol. 299 Jan. 2003; XP-002384365; www.sciencemag.org.
Relevant portion of European Search Report of corresponding European Application 04711724.7-2203.
Ma, L.P. et al.; "Organic Electrical Bistable Devices and Rewritable Memory Cells"; Applied Physics Letter; Apr. 22, 2002; pp. 2997-2999; vol. 80, No. 16; American Institute of Physics; USA.
Horiuchi, S. et al.; "Quantum Phase Transition in Organic Charge-Transfer Complexes"; Science; Jan. 10, 2003; pp. 229-232; vol. 299; American Association of Advanced Science; USA.
Kumai, et al, "Current-Inducing Metallization and Stripe Pattern Formation of K-TCNQ crystals", Kotai Butsuri, 35 (2000) 35, Partial English Translation.
Adachi, et al, Oyo Butsuri Gakkai Yokoshu, Mar. 2002, Third Issue, 27a-M-5, p. 1236.
Potember, R.S., et al, Electrical switching and memory phenomena in Cu-TCNQ thin films, Appl. Phys. Lett. 34(6), Mar. 15, 1979, p. 405-407.
Kawakami, H. et al., "Electric bistable characteristics of aminoimidazole carbonitrile," The Japan Society of Applied Physics and Related Societies No. 3, Issue date: Mar. 27, 2003, p. 1340. Abstract.
Ma, L.P. et al.; "Data Storage With 0.7 nm Recording Marks on a Crystalline Organic Thin Film by a Scanning Tunneling Microscope"; Applied Physics Letters; Aug. 10, 1998; vol. 73 No. 6,; p. 850-852.
Related co-pending U.S. Appl. No. 10/545,855; Kawakami et al.; Switching Element; filed Nov. 16, 2005; Spec. pp. 1-29; Figs. 1-8; Preliminary Amendment.
First Examination Report issued in corresponding European patent application No. 04711724.7-2203, dated Dec. 19, 2007.

* cited by examiner

SWITCHING ELEMENT

This application is a U.S. National Phase Application of PCT International Application PCT/JP2004/001750 which claims priority from Japanese Application Nos. 2003-038530 filed on Feb. 17, 2003 and 2003-341388 filed on Sep. 30, 2003.

TECHNICAL FIELD

The present invention relates to a switching element in which an organic bistable layer is disposed between two electrodes, this element being suitable as a switching element for driving an organic EL display panel or for a high-density memory.

BACKGROUND ART

In recent years, characteristics of organic electronic materials have been remarkably improved. In particular, among low-order conductors such as charge transfer complexes, there are materials having specific properties such as a metal-insulator transition, and application thereof to switching elements for driving an organic EL display panel or to high-density memories is being studied.

Organic bistable materials have attracted attention as materials that can be employed for the aforementioned switching elements. Organic bistable materials are organic materials demonstrating the so-called nonlinear response such that if a voltage is applied to the material, an electric current in a circuit rapidly increases at a voltage above a certain value and a switching phenomenon is observed.

FIG. 19 shows an example of the voltage-current characteristic of an organic bistable material demonstrating the above-described switching behavior.

As shown in FIG. 19, the organic bistable material has two current-voltage characteristics: a high-resistance characteristic 51 (OFF state) and a low-resistance characteristic 52 (ON state), and a nonlinear response characteristic such that if a bias Vb is applied in advance and then the voltage is raised to Vth2 (high transition voltage) or higher, a transition is made from the OFF state to the ON state, and if the voltage becomes equal to or less than Vth1 (low transition voltage), then a transition is made from the ON state to the OFF state and the resistance value changes. In other words, the so-called switching operation can be performed by applying a voltage of Vth2 or higher or Vth1 or lower to the organic bistable material. Here, Vth1, Vth2 can be also applied as pulse voltages.

A variety of organic complexes are known as the organic bistable materials demonstrating such nonlinear response. For example, R. S. Potember et al. fabricated a switching element having two stable resistance values with respect to a voltage by using a Cu-TCNQ (copper-tetracyanoquinodimethane) complex (R. S. Potember et al. Appl. Phys. Lett. 34, (1979) 405).

Further, Kumai et al. used a single crystal of a K-TCNQ (potassium-tetracyanoquinodimethane) complex and observed the switching behavior caused by the nonlinear response (Kumai et al. Kotai Butsuri, 35 (2000) 35).

Furthermore, Ando et al. formed a thin film of a Cu-TCNQ complex by using a vacuum vapor deposition method, clarified switching characteristics thereof and investigated the possibility of application to an organic EL matrix (Ando et al. Preprints of Applied Physics Association Conference, Spring 2000, Vol. 3, 1236).

Further, Yang Yang et al. disclosed that a bistable characteristic for a memory element can be obtained by forming a thin film of a material with a high electric conductivity such as gold, silver, aluminum, copper, nickel, magnesium, indium, calcium, or lithium or introducing it as dispersed fine particles in a material with a low electric conductivity such as aminoimidazole carbonitrile (AIDCN), alumiquinoline, polystyrene, and polymethyl methacrylate (PMMA) and that even if the applied voltage is zero, the preceding ON/OFF state can be stored (PCT Application No. 02/37500).

However, the above-described switching elements using organic charge transfer complexes have the following problems. Thus, because the organic bistable material is a charge transfer complex, it is a material of a two-component system comprising a combination of a molecule with donor properties or a metal element having donor properties and a molecule with acceptor properties such as TCNQ.

For this reason, the composition ratio of the two components has to be strictly controlled when the switching element is fabricated. Thus, in the charge transfer complexes of a two-component system, for example, as shown in FIG. 20, donor molecules and acceptor molecules are stacked as respective columns and form a donor molecule column 61 and an acceptor molecule column 62 and a bistable characteristic is demonstrated because the components of each column carry out a partial charge transition between the molecules (or metal atoms). Therefore, when the composition ratio of the two components is too high or too low, a significant effect is produced on the bistable characteristic of the entire material.

Therefore, in the above-mentioned Cu-TCNQ complex, if the composition ratio of Cu and TCNQ differs, it causes changes in crystallinity and electric characteristics of the materials and a spread in the bistability characteristic. In particular, when a film is formed by a vacuum vapor deposition method or the like, a uniform film is difficult to form over a large surface area because of the difference in vapor pressure between the two components or due to a geometric arrangement employed when separate deposition sources are used for both materials in a co-deposition method. Therefore, in the organic bistable materials in prior arts, there is a problem that it is difficult to mass-produce a switching element having a uniform bistable characteristic and product quality. A switching element formed of organic transfer complexes, as shown in FIG. 19, has a problem that transition voltage th2 is high, about 10 V when transition is made from OFF state to the ON state, but the cyclic performance is poor.

Further, the following problem is associated with the switching element described in PCT application No. 02/37500. Though cyclic performance of the element is good, the voltage Vth2 of transition from the OFF state to the ON state shown in FIG. 19 is very low (about 3 V). In particular, the transition voltage is too low in applications to a display drive such as organic EL displays.

The present invention was created to resolve the above-described problems of the conventional technology and it is an object thereof to provide a switching element in which fluctuations of material composition can be inhibited and a uniform bistable characteristic can be obtained, this switching element being suitable for mass production, having a high transition voltage, and demonstrating excellent cyclic performance.

DISCLOSURE OF THE INVENTION

One switching element in accordance with the present invention is a switching element having two stable resistance values with respect to the voltage applied between electrodes, wherein a first electrode layer, an organic bistable material layer, and a second electrode layer are successively formed as thin films on a substrate and the organic bistable material constituting the organic bistable material layer is a quinomethane-based compound represented by the general formula (I) below.

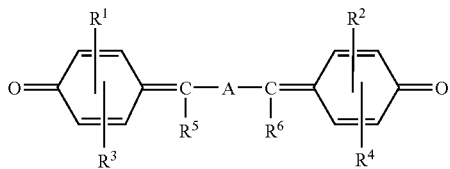

(in Formula (1), each of R1-R4 represents a group selected from a hydrogen atom, an optionally substituted C1-6 alkyl group, and an optionally substituted aryl group, where R1-R4 may be same or different. Each of R5 and R6 represents an optionally substituted aryl group or an optionally substituted hetero ring, where R5, R6 may be same or different. A represents a group selected from groups (1)-(10) shown below.)

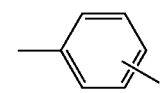

(1)

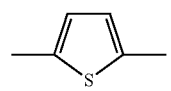

(2)

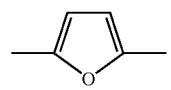

(3)

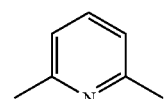

(4)

(5)

(6)

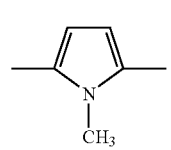

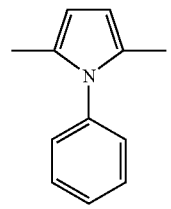

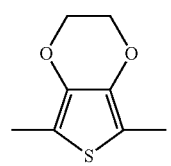

(7)

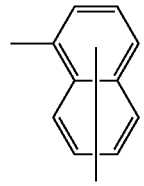

(8)

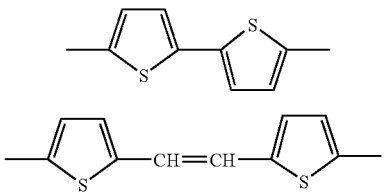

(9)

(10)

With this switching element, electron transfer ability is provided and excellent bistability is obtained because the above-described quinomethane-based compound of Formula (I) has a quinone group, which is an electron-accepting functional group. In addition, the switching element has an appropriate metal diffusion rate. Therefore, it can be advantageously used for the present invention.

Further, because the quinomethane-based compound of Formula (I) has a high ratio of a low-resistance state to a high-resistance state, it demonstrates excellent bistable suitability. Furthermore, because a thin film can be easily formed by a vapor deposition method or the like, this compound can be especially advantageously used as an organic bistable material.

Another switching element in accordance with the present invention is a switching element having two stable resistance values with respect to a voltage applied between electrodes, wherein a first electrode layer, an organic bistable material layer, and a second electrode layer are successively formed as thin films on a substrate and the organic bistable material constituting the organic bistable material layer is a monoquinomethane-based compound represented by the general formula (II) below.

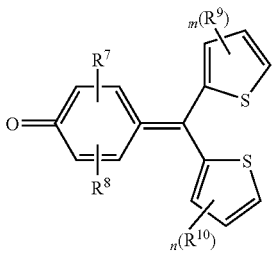

(II)

(in Formula (II), each of R7-R10 represents a group selected from a hydrogen atom, a halogen atom, an optionally substituted C1-6 alkyl group, and an optionally substituted aryl groups, where R7-R10 may be same or different; m and n are integers of 0 to 3).

With this switching element, electron transfer ability is provided and excellent bistability is obtained because the above-described monoquinomethane-based compound of Formula (II) has a quinone group, which is an electron-accepting functional group. In addition, the switching element has an appropriate metal diffusion rate. Therefore, it can be advantageously used for the present invention.

Further, because the monoquinomethane-based compound of Formula (II) has a high ratio of a low-resistance state to a high-resistance state, it demonstrates excellent bistable suitability. Furthermore, because a thin film can be easily formed by a vapor deposition method or the like, this compound can be especially advantageously used as an organic bistable material.

Yet another switching element in accordance with the present invention is a switching element having two stable resistance values with respect to a voltage applied between electrodes, wherein a first electrode layer, an organic bistable material layer, and a second electrode layer are successively formed as thin films on a substrate and a metal constituting the second electrode layer is diffused into the organic bistable material layer.

In this case, it is preferred that a diffusion inhibiting layer comprising an organic bistable material different from the aforementioned organic bistable material layer be formed between the organic bistable material layer and at least one of the first electrode layer and second electrode layer, and the other organic bistable material be a material where a diffusion rate of the metal of the second electrode layer is lower than that in the organic bistable material layer.

With this switching element the diffused metal can be considered to behave as an acceptor. As a result, both the lowest unoccupied orbital level and the highest occupied orbital level of the diffusion zone are supposedly high. Therefore, because the diffusion zone of the metal becomes an energy barrier, a large electric field is necessary due to switching and the transition voltage apparently increases. Furthermore, because switching is not accompanied by the phase change, the cyclic performance is good.

Further, with the mode in which the above-described diffusion inhibiting layer is formed, the decrease in the resistance of the organic bistable material layer and increase in leakage current caused by excessive diffusion of the metal to the organic bistable material layer can be prevented and the leakage current can be suppressed.

In accordance with the present invention, it is preferred that the second electrode layer be formed by vapor deposition and the temperature of the substrate during the vapor deposition be 30-150° C. In this case, setting the substrate temperature during vapor deposition within this range increases the diffusion rate of the metal. Therefore, the metal constituting the second electrode layer can sufficiently diffuse into the organic bistable material layer.

Further, in accordance with the present invention, it is preferred that the second electrode layer comprise at least one species selected from gold, platinum, rhodium, silver, and chromium. The absolute value of the work function of those metals is the highest among the electrode materials and they easily behave as acceptors during diffusion into the organic bistable material. Therefore, they can be advantageously used for the present invention.

BEST MODE FOR CARRYING OUT THE INVENTION

Figure 1:
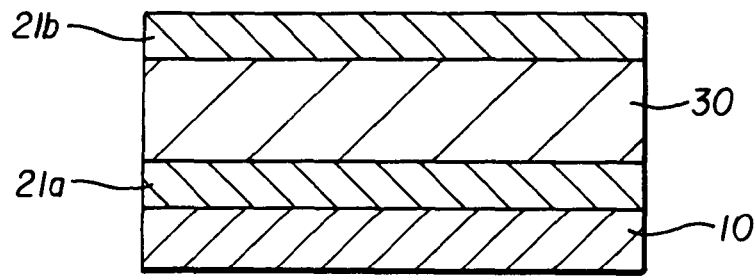
FIG. 1 is a schematic structural drawing illustrating an embodiment of the switching element of the present invention.

The present invention will be described below in greater detail with reference to the drawings. FIG. 1 is a schematic structural drawing illustrating an embodiment of the switching element of the present invention.

As shown in FIG. 1, the switching element has a configuration in which a first electrode layer 21a, an organic bistable material layer 30, and a second electrode layer 21b are successively laminated on a substrate 10.

No specific limitation is placed on the material for the substrate 10, but a conventional well-known glass substrate is preferably used therefor.

No specific limitation is placed on the material for the first electrode layer 21a formed on the substrate 10 and metal materials such as aluminum, gold, silver, chromium, nickel, and iron, inorganic materials such as ITO and carbon, conjugated organic materials, organic materials such as liquid crystals, and semiconductor materials such as silicon can be appropriately selected therefor. A conventional well-known method such as a vacuum vapor deposition method is preferably used as the method for forming the first electrode layer 21a, but this selection is not limiting.

When the first electrode layer 21a is formed by vacuum vapor deposition, the substrate temperature during vapor deposition is appropriately selected according to the electrode material used, the preferred range being 0-150° C. The film thickness is preferably 50-200 nm.

The organic bistable material layer 30 is formed as a thin film on the first electrode layer 21a. A compound having a functional group for transporting the electric charge and comprising an electron-donating functional group and an electron-receiving functional group in a molecule is preferably used as the organic bistable material used in the organic bistable material layer 30.

Examples of electron-donating functional groups include —SCH3, —OCH3, —NH2, —NHCH3, and —N(CH3)2, and examples of electron-accepting functional groups include —CN, NO2, —CHO, —COCH3, —COOC2H5, —COOH, —Br, —Cl, —I, —OH, —F, and =O.

Examples of such compounds comprising an electron-donating functional group and an electron-receiving functional group in a molecule include aminoimidazole-based compounds, dicyano-based compounds, pyridon-based compounds, styryl-based compounds, stilbene-based compounds, quinomethane-based compounds, and butadiene-based compounds.

In accordance with the present invention, a quinomethane-based compound represented by the general formula (I) below is preferred as a compound having the above-described electron-donating functional group and the above-described electron-accepting functional group in a molecule.

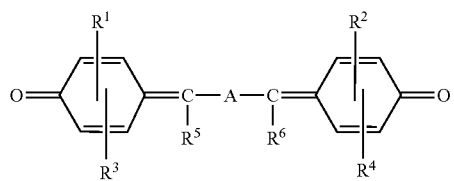

(I)

(in Formula (1), each of R1-R4 represents a group selected from a hydrogen atom, an optionally substituted C1-6 alkyl group, and an optionally substituted aryl group, where R1-R4 may be same or different. R5, R6 represent an optionally substituted aryl group or an optionally substituted hetero ring, where R5, R6 may be same or different. A represents a group selected from groups (1)-(10) shown below.)

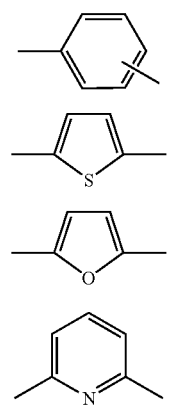

(1)

(2)

(3)

(4)

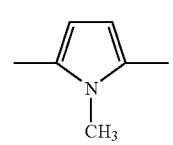

(5)

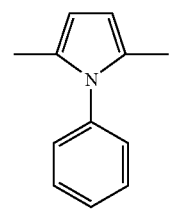

(6)

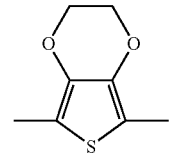

(7)

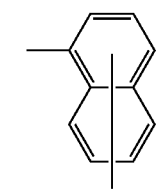

(8)

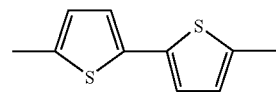

(9)

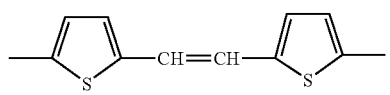

(10)

This quinomethane-based compound (I) can be synthesized according to the reaction formula shown below. The compound shown below is an example with the above-mentioned A being (2) or (3)(X is represents oxygen or sulfur).

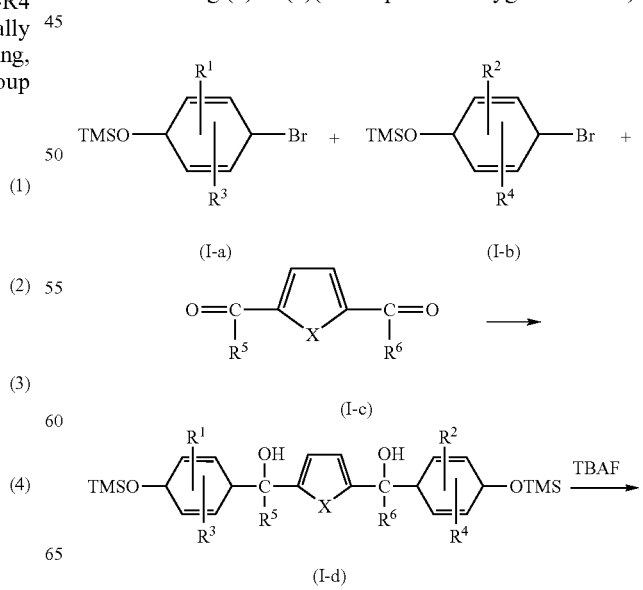

-continued

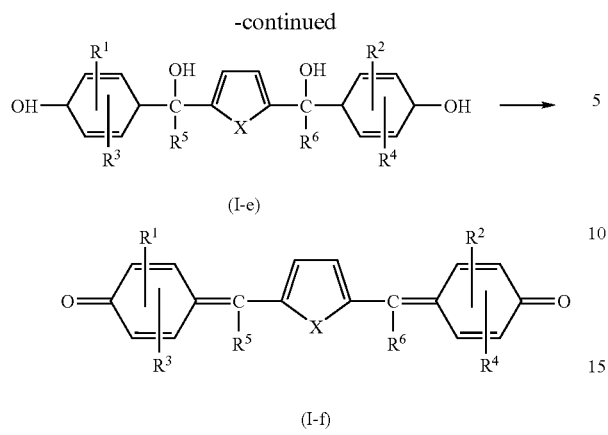

(I-e)

(I-f)

Thus, a compound (I-e) can be synthesized by reacting a compound (I-a) and a compound (I-b) with a compound (I-c) in the presence of an appropriate organometallic catalyst, for example, n-butyllithium to obtain a compound (I-d) and removing TMS (trimethylsilyl group) that is a protective group. Then, a quinomethane-based compound (I-f) can be obtained by further subjecting the compound (I-e) to dehydration condensation in the presence of a catalyst, for example, p-toluenesulfonic acid. TBAF in the reaction formula above represents tetrabutylammonium fluoride. This synthesis method is described in detail, for example, in JP-A Nos.-2003-228185, 2003-238561, and 2003-105039.

Specific examples of the aforementioned quinomethane-based compounds are represented, for example, by the following structural formulas (I-1)-(I-32).

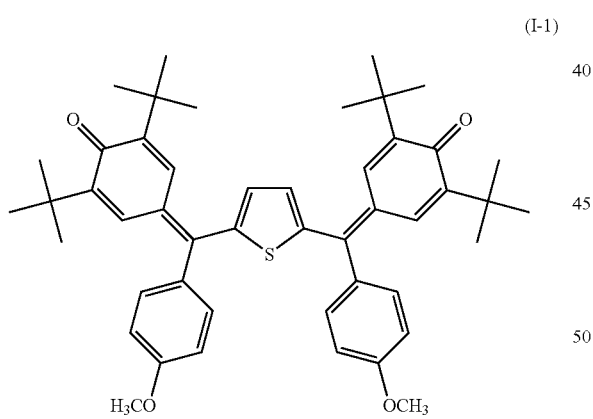

(I-1)

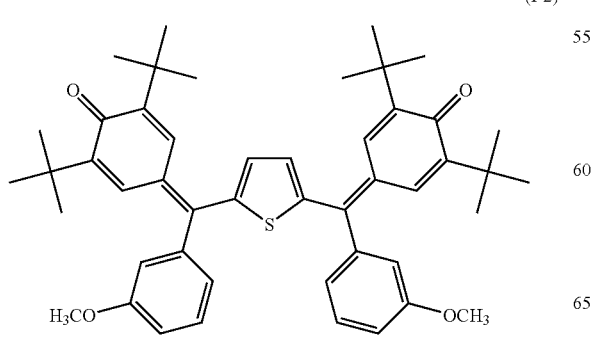

(I-2)

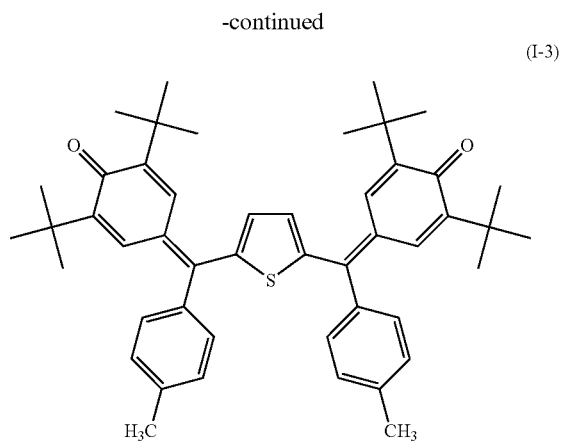

(I-3)

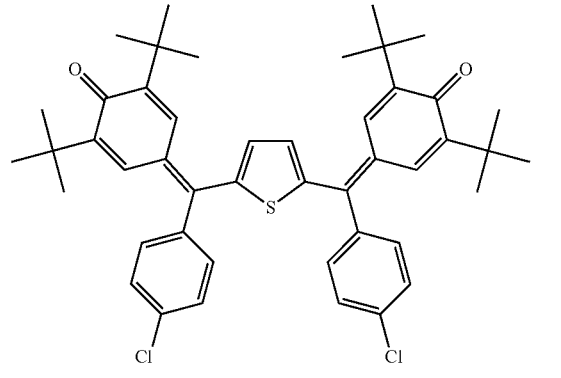

(I-4)

(I-5)

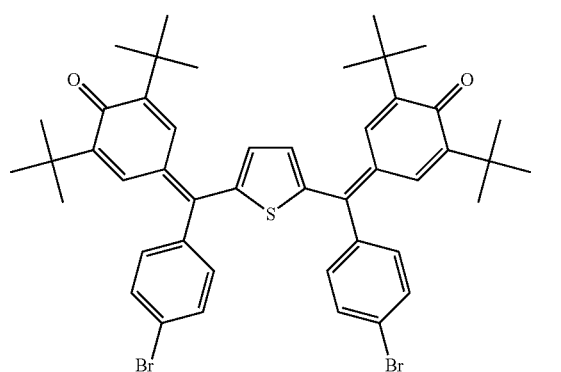

(I-6)

-continued
(I-7)
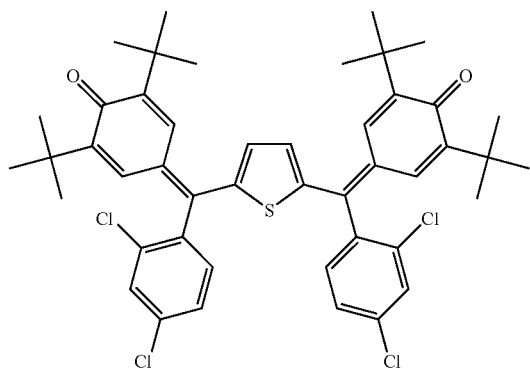
(I-8)
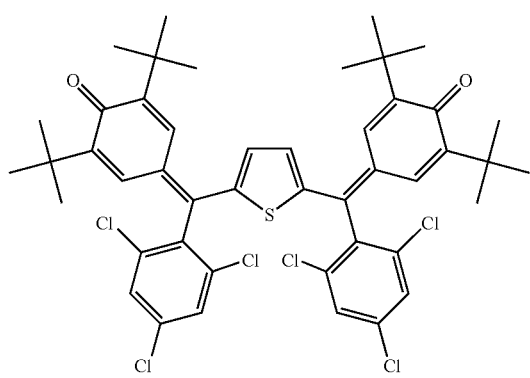
(I-9)
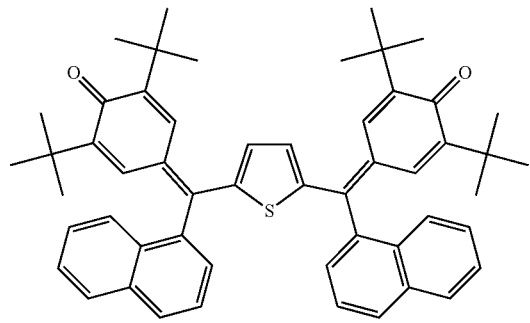
(I-10)
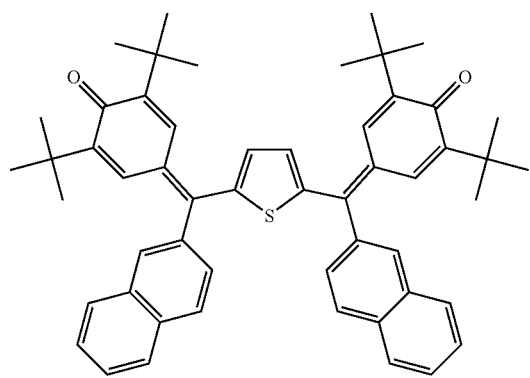
-continued
(I-11)
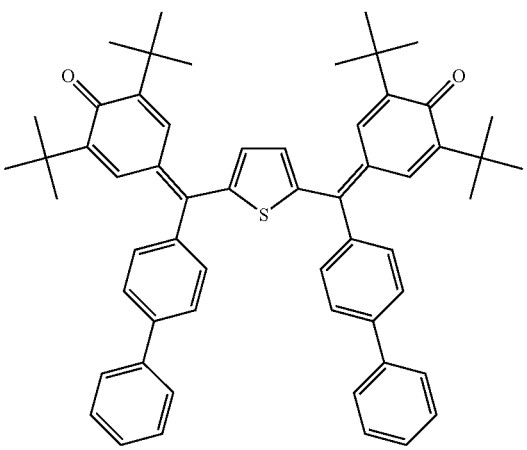
(I-12)
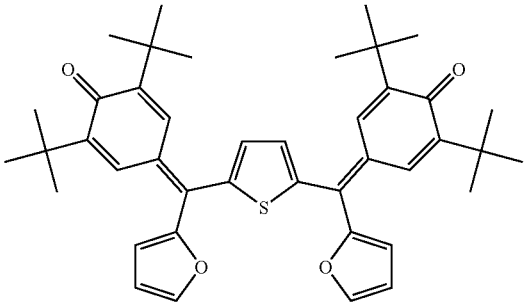
(I-13)
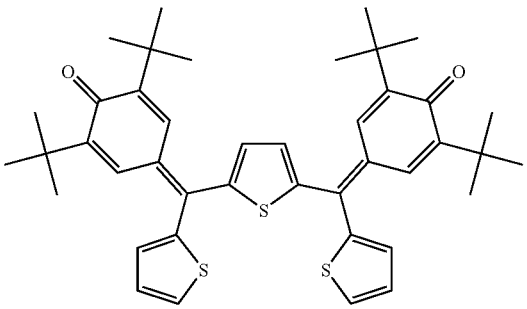
(I-14)
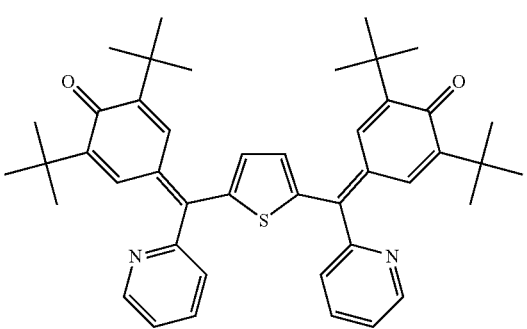

-continued
(I-15)
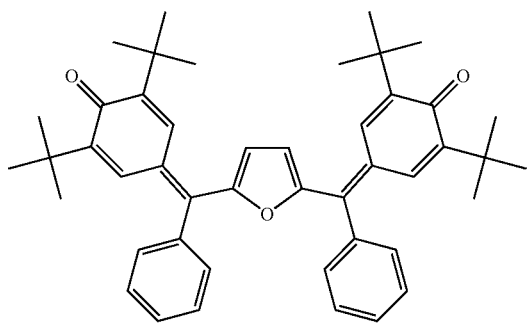
(I-16)
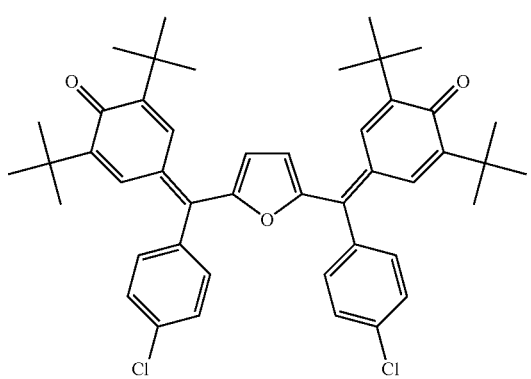
(I-17)
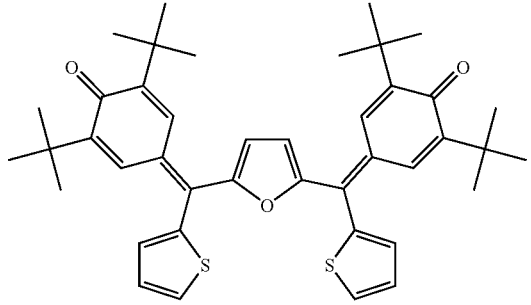
(I-18)
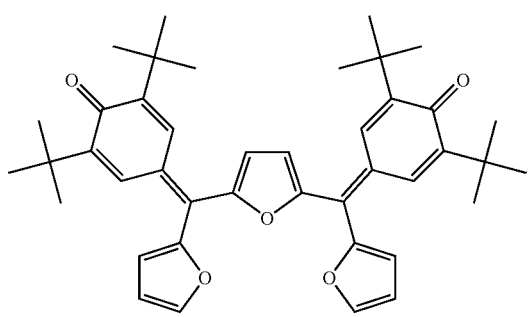
-continued
(I-19)
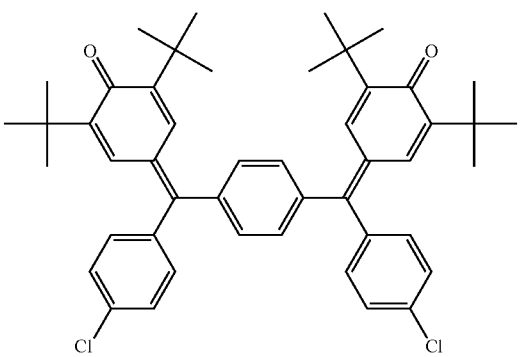
(I-20)
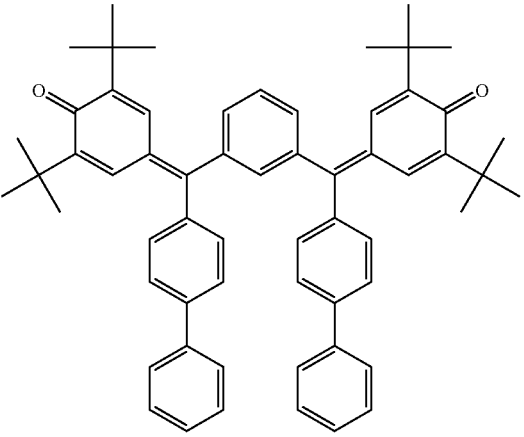
(I-21)
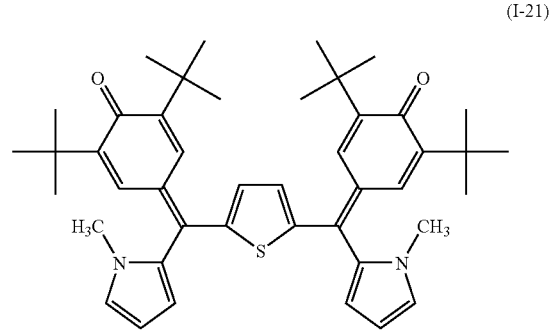
(I-22)
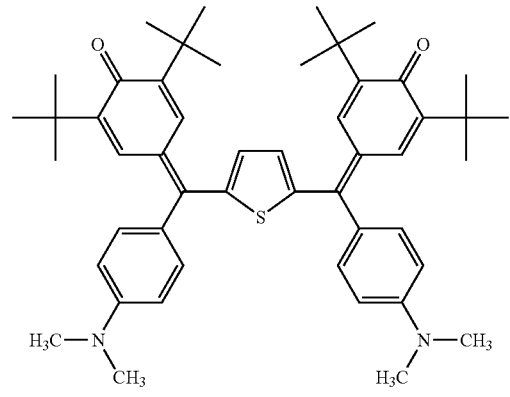

-continued
(I-23)
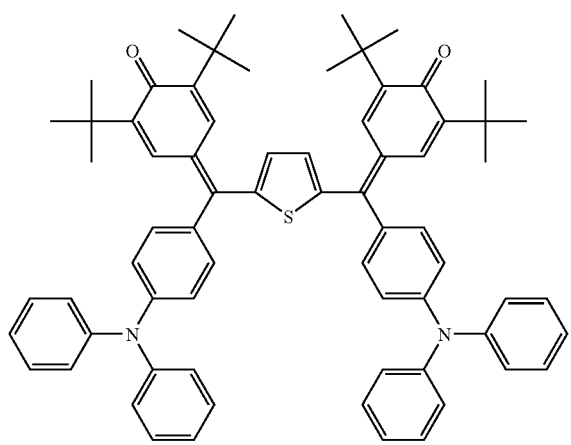
(I-24)
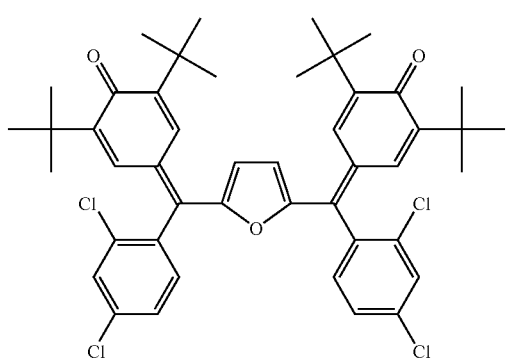
(I-25)
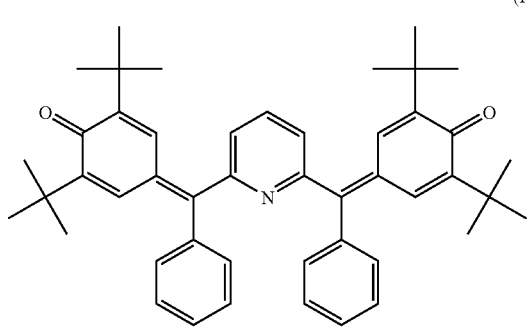
(I-26)
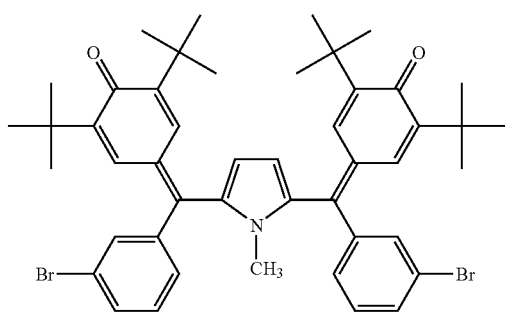
(I-27)
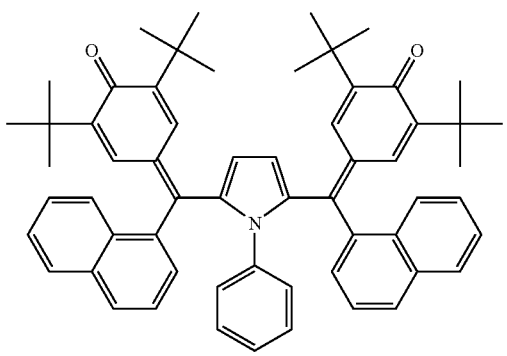
(I-28)
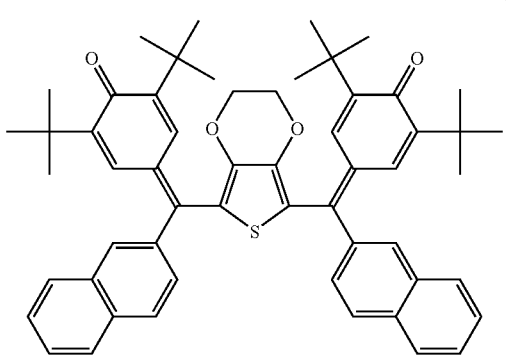
(I-29)
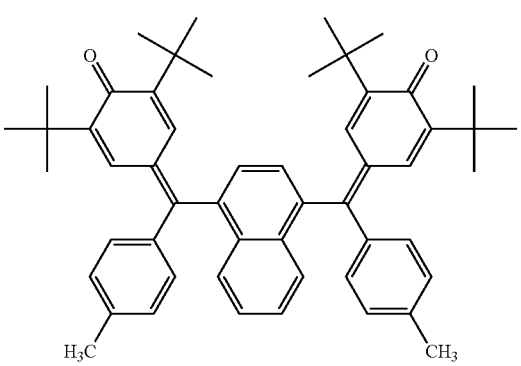
(I-30)
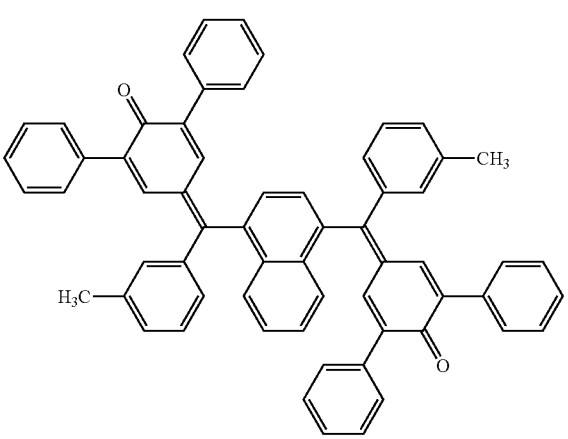

-continued (I-31)

(I-32)

(in the compounds I-1 to I-32 above, symbol "+" of substitution group represents a t-butyl group).

Further, a monoquinomethane-based compound represented by the following structural formula (II) may be used as the organic bistable material.

(II)

(in Formula (II), each of R7-R10 represents a group selected from a hydrogen atom, a halogen atom, an optionally substituted C1-6 alkyl group, and an optionally substituted aryl group, where R7-R10 may be same or different; m and n are integers of 0 to 3).

Specific examples of the aforementioned monoquinomethane-based compound are represented, for example, by the following structural formulas (II-1)-(II-12).

(II-1)

(II-2)

(II-3)

(II-4)

(II-5)

(II-6)

(II-7)

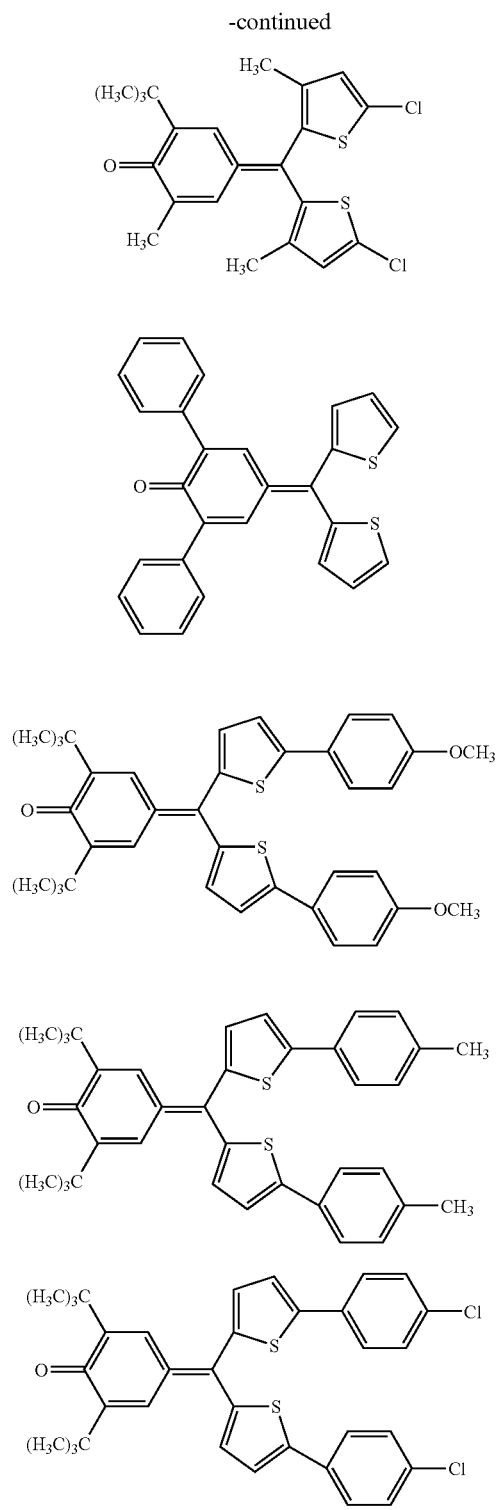

The monoquinomethane-based compound of the general formula (II) shown hereinabove can be synthesized, for example, according to the reaction formula shown hereinbelow. The example shown below relates to synthesizing the compound represented by the structural formula (II-1) shown above, but compounds of other structures can be synthesized by the same method.

Thus, for example, 29 mmol (18 mL) of 1.6 M n-butyllithium hexane solution (BuLi) is dropwise added under a nitrogen atmosphere at −78° C. to a THF solution of 24 mmol (8.6 g) of 4-bromo-2,6-di-t-butyl-1-[trimethylsilyl]benzene (structural formula (A-1)). Then, a compound of structural formula (C-1) is obtained by adding 20 mmol (3.9 g) of dithienyl ketone (structural formula (B-1)) and stirring at room temperature.

An aqueous solution of ammonium chloride and then 24 mmol (24 mL) of 1.0 M THF solution of tetrabutylammonium fluoride (TBAF) are thereafter dropwise added to obtain a compound of structural formula (D-1). Then, a compound of structural formula (II-1) can be obtained by adding a small quantity of p-toluenesulfonic acid monohydrate (p-TsOH), refluxing under heating, distilling the solvent off, and recrystallizing the solids in a mixed solvent of chloroform and hexane.

Here, 4-bromo-2,6-di-tert-butyl-1-[trimethylsilyl]benzene (structural formula (A-1)) can be synthesized, for example, by a well-known method described in JP-A-2003-238561. Furthermore, di-2-thienyl ketone (structural formula (B-1)) is readily available from Sigma-Aldrich Japan Co.

Further, the yield of the compound obtained by the above-described synthesis method was 3.3 g (yield 43.2%), MS m/z 382 (M+) result was obtained by mass spectrometry, and the structure represented by the structural formula (II-1) shown above was confirmed.

No specific limitation is placed on the method for forming the organic bistable material layer 30, and methods such as vacuum vapor deposition method, spin coating method, electrolytic polymerization method, chemical vapor deposition method (CVD)), monomolecular film deposition method (LB method), dipping method, bar coating method, ink jet printing method, and screen printing method can be used.

When the organic bistable material layer 30 is formed by vacuum vapor deposition, the substrate temperature during vapor deposition is selected appropriately according to the organic bistable material used, but is preferably 1-100° C. Further, the film thickness is preferably 20-150 nm.

When the organic bistable material layer 30 is formed by coating, for example, by a spin coating method, halogenides such as dichloromethane, dichloroethane, and chloroform, ethers such as tetrahydrofuran (THF) and ethylene glycol dimethyl ether, aromatic compounds such as toluene and xylene, alcohols such as ethyl alcohol, esters such as ethyl acetate and butyl acetate, ketones such as acetone, MEK, and also acetonitriles can be advantageously used as solvents for coating. A coating liquid is prepared by dissolving the organic bistable material within a range of 0.001-30 wt. % in the aforementioned solvent and adding, if necessary, a binder resin. For example, polycarbonates, polyesters, polyvinyl alcohol, and polystyrene can be used as the binder resin. Spin coating conditions can be appropriately set according to the target film thickness, but the preferred range of the rotation rate is 200-3600 rpm.

The second electrode layer 21b is formed on the organic bistable material layer 30. A metal constituting the second electrode layer 21b is diffused into the organic bistable material layer 30.

Among the electrode materials, one species selected from gold, platinum, rhodium, and silver is preferably used as the second electrode layer 21b. This is because those materials have a high absolute value of work function and easily behave as acceptors when they are diffused into the organic bistable material. Among them, gold is especially preferred. The preferred thickness of the second electrode layer 21b is 50-200 nm.

For example, a method comprising forming the second electrode layer 21b by vapor deposition such as vacuum vapor deposition in the same manner as the first electrode layer 21a, with the temperature of the substrate 10 being 30-150° C. during this vapor deposition, can be used for causing the diffusion of the metal constituting the second electrode layer 21b in the organic bistable material layer 30. With the substrate temperature within this temperature range, the metal is diffused into the organic bistable material layer 30 simultaneously with vapor deposition. Therefore, a separate diffusion process becomes unnecessary. It is undesirable that the substrate temperature be less than 30° C., because the diffusion of the metal constituting the second electrode layer 21b in the organic bistable material layer 30 becomes insufficient.

Furthermore, if the temperature is higher than 150° C., it exceeds the glass transition temperature of the organic bistable material layer. This is undesirable because the thin film crystallizes, thereby causing cohesion, peeling, and the like.

Further, the above-described method of diffusing the metal in the organic bistable material layer 30 is not limiting, and the diffusion of the metal may be also conducted by forming the second electrode layer 21b by vapor deposition or the like and then heating the second electrode layer 21b.

Further, from the standpoint of suppressing the below-described leakage current, the diffusion depth of the metal into the organic bistable material layer 30 is preferably such that the metal diffuses only to a certain intermediate location, rather than through the entire organic bistable material layer 30. More specifically, the diffusion from the side of the second electrode layer 21b preferably proceeds to 5-70% of the entire thickness of the organic bistable material layer 30. It is undesirable that the diffusion depth be less than 5% because the diffusion is insufficient and the increase in transition voltage is not demonstrated. Conversely, it is undesirable that the diffusion depth be more than 70% because the below-described leakage current increases.

The diffusion of the metal to the organic bistable material layer 30 can be confirmed, for example, by conducting cross-sectional observations with TEM (transmission electron microscope) or metal composition analysis of the cross section with TEM-EPMA (transmission electron microscope—electron microanalyzer).

Figure 2:
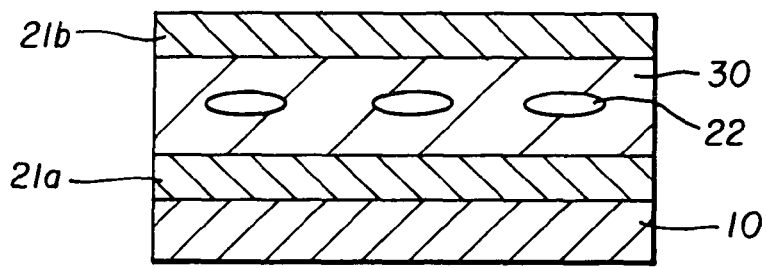
FIG. 2 is a schematic structural drawing illustrating another embodiment of the switching element of the present invention.
Figure 3:
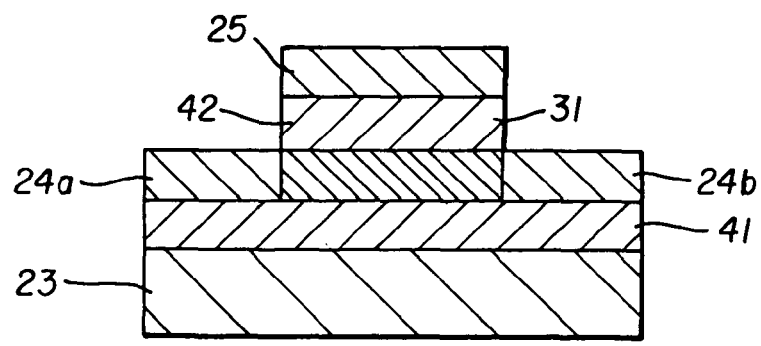
FIG. 3 is a schematic structural drawing illustrating yet another embodiment of the switching element of the present invention.

The configuration of the switching element in accordance with the present invention is not limited to the configuration shown in FIG. 1 and may be, for example, as shown in FIG. 2 and FIG. 3.

The embodiment illustrated by FIG. 2 differs from the above-described embodiment shown in FIG. 1 in that a three-terminal element is obtained by additionally providing a third electrode 22 in the organic bistable material layer 30. As a result, it is possible to use the electrode layers 21a, 21b as the electrodes for passing an additional electric current, apply the above-described bias Vb shown in FIG. 19, use the third electrode 22 as an electrode for controlling the resistance state of the bistable material layer 30, and apply a low threshold voltage Vth1 or high threshold voltage Vth2 shown in FIG. 19.

Further, in the embodiment shown in FIG. 3, a four-terminal element is obtained by forming an insulating layer 41 on the second electrode layer 23, then forming an organic bistable material layer 31 and electrode layers 24a, 24b on both sides, so as to sandwich the organic bistable material layer 31, on the insulating layer 41, and then successively forming an insulating layer 42 and a fourth electrode layer 25 on the bistable material layer 31.

More specifically, in this switching element, for example, the third electrode 23 can be a silicon substrate, the insulating layers 41, 43 can be vapor deposited films of metal oxides, and the electrode layers 24a, 24b and the fourth electrode 25 can be vapor deposited aluminum films. The resistance state of the organic bistable material layer 31 can be controlled by using the electrode layers 24a, 24b as electrodes for passing an additional electric current, applying the above-described bias Vb shown in FIG. 19, and then applying an electric field to the organic bistable material layer 31 with the third electrode 23 and fourth electrode 25.

Figure 4:
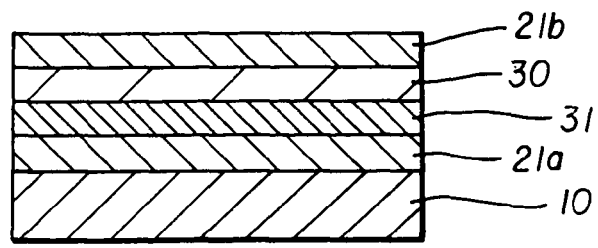
FIG. 4 is a schematic structural drawing illustrating yet another embodiment of the switching element of the present invention.

FIG. 4 shows another embodiment of the present invention. In the explanation of the below-described embodiment, components identical to those of the above-described embodiment are assigned with the same symbols and the explanation thereof is omitted.

The difference between the present embodiment and the above-described embodiment is in that a diffusion inhibiting layer 31 is provided between the first electrode layer 21a and the organic bistable material layer 30 in the present embodiment.

The diffusion inhibiting layer 31 comprises an organic bistable material different from that of the organic bistable material layer 30. This other organic bistable material is a material where the diffusion rate of the metal of the second electrode layer 21b is lower than that in the organic bistable material layer 30. The presence of the diffusion inhibiting layer 31 prevents the metal from diffusing excessively into the organic bistable material layer 30, the resistance of the organic bistable material layer 30 from decreasing, and the leakage current from increasing and makes it possible to control the leakage current.

For example, a combination of a dicyano-based compound or carbonitrile-based compound with a high diffusion rate of the metal as an organic bistable material in the organic bistable material layer 30 and a quinomethane-based compound with a low diffusion rate of the metal as another organic bistable material in the diffusion inhibiting layer 31 can be used as the combination of organic bistable materials of the organic bistable material layer 30 and diffusion inhibiting layer 31.

The diffusion inhibiting layer 31 can be formed by the method identical to that used for forming the above-described organic bistable material layer 30. The thickness of the diffusion inhibiting layer 31 is preferably 3-100 nm.

This diffusion inhibiting layer may be provided between the organic bistable material layer 30 and the first electrode layer 21a, as shown in FIG. 4, or between the organic bistable material layer 30 and the second electrode layer 21b, or in both locations.

With the switching element in accordance with the present invention that has the above-described configuration, cyclic performance is good and a high transition voltage is obtained. The following reasons can be suggested to explain those results.

In the above-described conventional switching element using TCNQ, the switching principle is based on charge transfer in the metal-TCNQ complex. Therefore, a phase change inevitably occurs, apparently causing poor cyclic performance. Furthermore, in the switching element of PCT Application No. 02/37500, the switching principle is considered to be based on fine metal particles and switching is not accompanied by such a phase change of the TCNQ system. As a result, cyclic performance is good, but the transition voltage is not easy to control.

By contrast, in the switching element in accordance with the present invention, the lowest unoccupied orbital level (LUMO level) of the organic bistable material is higher than the work function of the electrodes, and the switching principle is apparently based on local electric field concentration and charge injection caused by the tunnel effect induced by this electric field concentration.

Further, because the metal of the second electrode diffuses into the organic bistable material, the diffused metal apparently behaves as an acceptor. For this reason, both the LUMO level and the HOMO level (highest occupied orbital level) increase.

Figure 5:
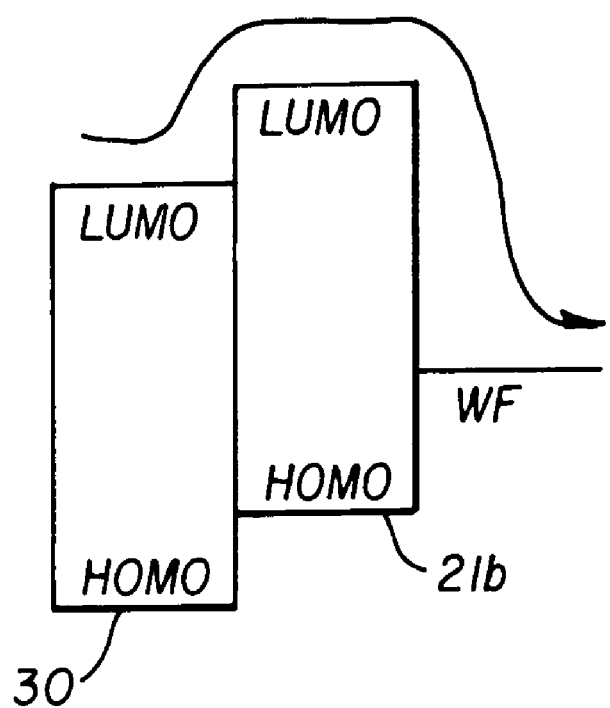
FIG. 5 is an explanatory drawing showing energy levels in the switching element of the present invention.
Figure 6:
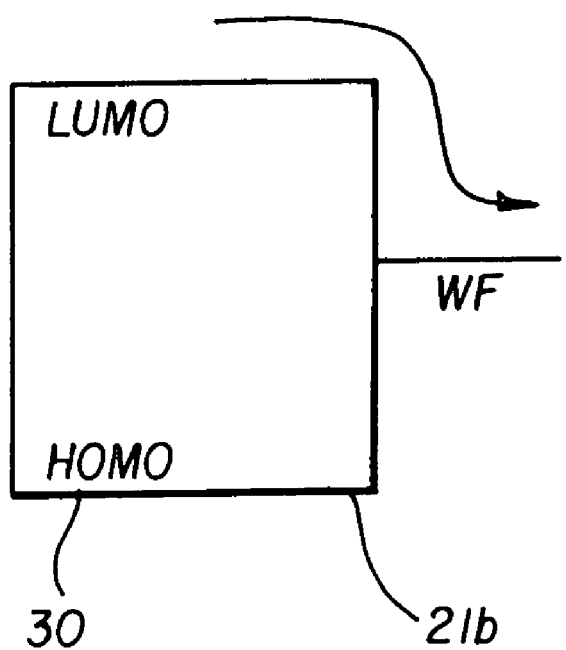
FIG. 6 is an explanatory drawing showing energy levels in the conventional switching element.

Thus, as shown by the energy band diagram relating to the interface of the organic bistable material layer 30 and the second electrode layer 21b in FIG. 5, in the switching element in accordance with the present invention, there is an increase in the energy level induced by metal diffusion (diffusion layer in FIG. 5). Comparison with the diagram shown in FIG. 6 where no metal diffusion layer is present suggests that in FIG. 5 the zone with metal diffusion serves as an energy barrier. As a result, a larger electric field is apparently necessary due to switching and the transition voltage increases. Furthermore, because this switching is not accompanied by phase change, cyclic performance is also good. In FIGS. 5 and 6, LUMO stands for the lowest unoccupied orbital, HOMO—the highest occupied orbital, and WF—the work function.

As described hereinabove, the present invention can provide a switching element in which fluctuations of material composition can be inhibited and a uniform bistable characteristic can be obtained, this switching element being suitable for mass production, having a high transition voltage and demonstrating excellent cyclic performance. Therefore, this switching element can be advantageously used as a switching element for driving an organic EL display panel or for a high-density memory.

The switching element in accordance with the present invention will be described below in greater detail by using working examples thereof.

WORKING EXAMPLE 1

The switching element with a configuration shown in FIG. 1 was produced by the following procedure.

The switching element was formed by using a glass substrate as the substrate 10 and successively forming thin films by vacuum vapor depositing aluminum as the first electrode layer 21a, a quinomethane-based compound as the bistable material layer 30, and gold as the second electrode layer 21b. The compound with the below-described structural formula (I-1) was used as the quinomethane-based compound.

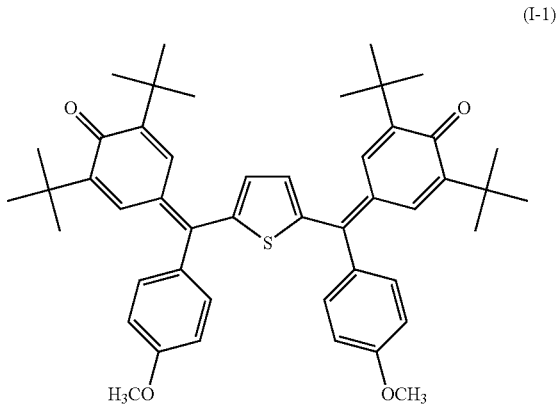

(I-1)

Further, the first electrode layer 21a, organic bistable material layer 30, and second electrode layer 21b were formed to have a thickness of 100 nm, 80 nm, and 100 nm, respectively. The vapor deposition apparatus performed diffusion pump gas discharge to a degree of vacuum of 3×10-6 Torr. Vapor deposition of aluminum and quinomethane-based compound was conducted at a substrate temperature of 20° C. and a film growth rate of 3 Å/sec and 2 Å/sec, respectively. Further, gold deposition was conducted by raising the substrate temperature to 50° C. and growing the film at a rate of 3 Å/sec by a resistance heating method. Vapor deposition of each layer was conducted continuously in the same vapor deposition apparatus under conditions preventing contact of samples with the air during vapor deposition.

WORKING EXAMPLE 2

A switching element was obtained by using the compound with the structural formula (I-13) presented below as the quinomethane-based compound and growing films under the same conditions as in Working Example 1 so that the first electrode layer 21*a*, organic bistable material layer 30, and second electrode layer 21*b* had a thickness of 100 nm, 80 nm, and 100 nm, respectively.

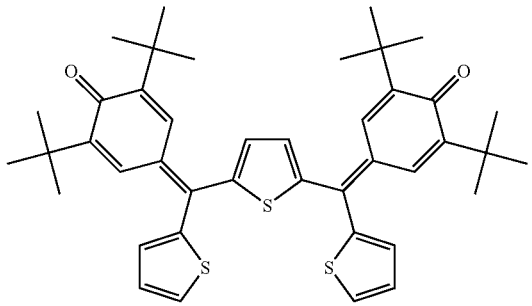

(I-13)

WORKING EXAMPLE 3

In Working Example 3, a switching element was obtained under the same conditions as in Working Example 1, except that vapor deposition of aluminum, quinomethane-based compound and gold was conducted at a substrate temperature of 20° C.

TEST EXAMPLE 1

Figure 7:
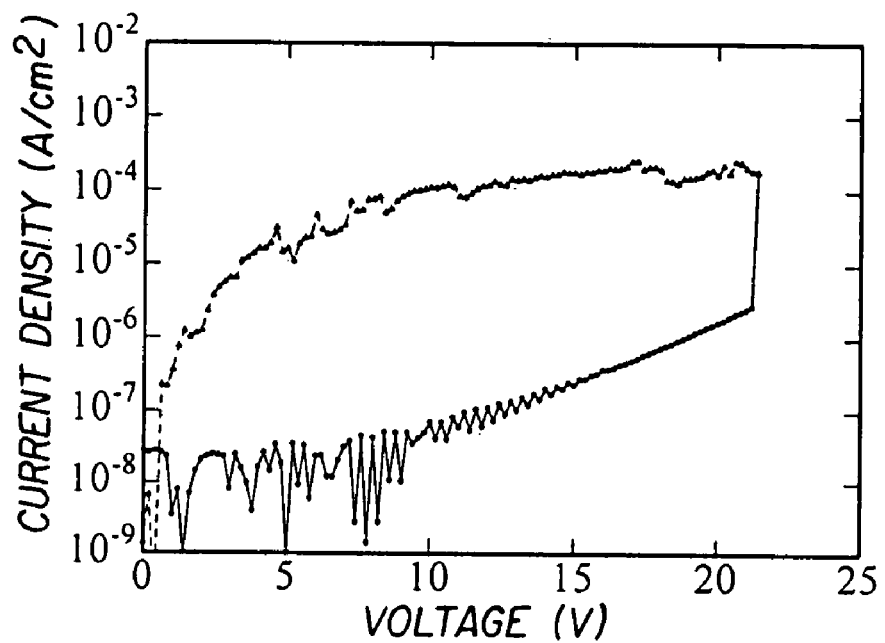
FIG. 7 is a diagram showing a current-voltage characteristic of a switching element in Working Example 1.
Figure 8:
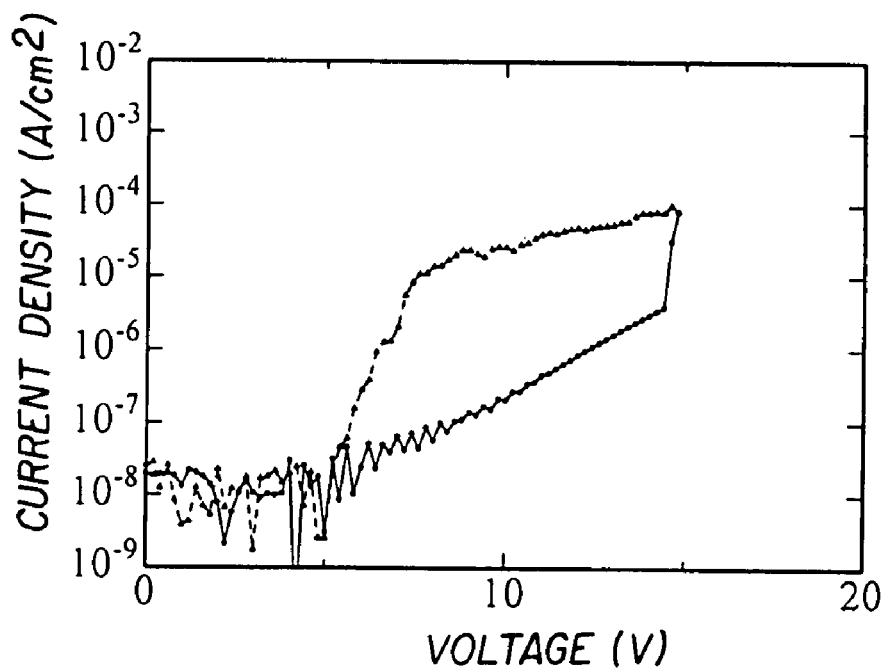
FIG. 8 is a diagram showing a current-voltage characteristic of a switching element in Working Example 2.
Figure 9:
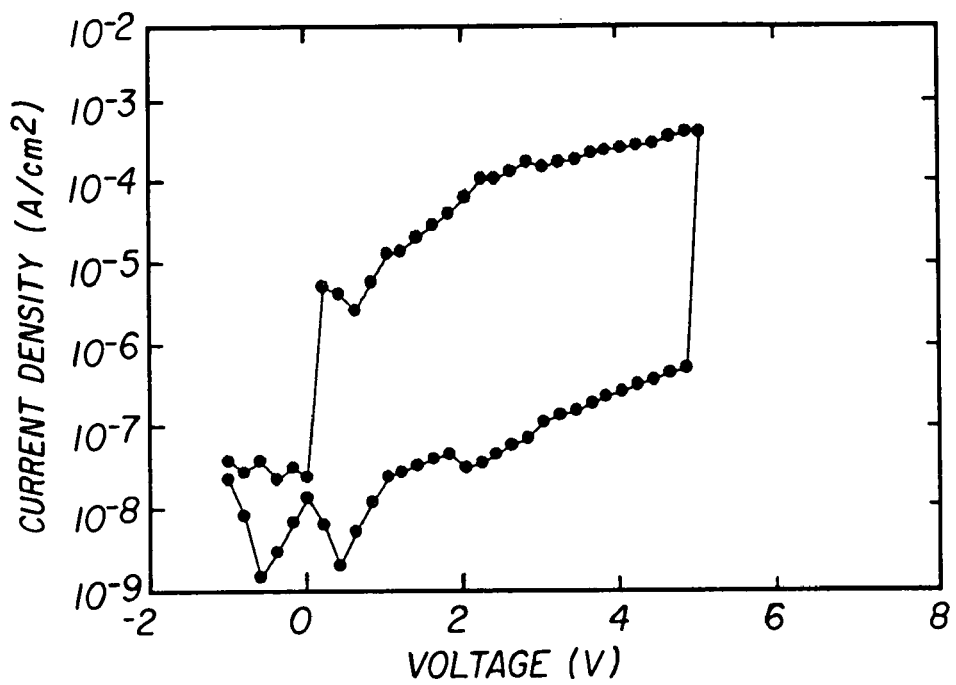
FIG. 9 is a diagram showing a current-voltage characteristic of a switching element in Working Example 3.
Figure 19:
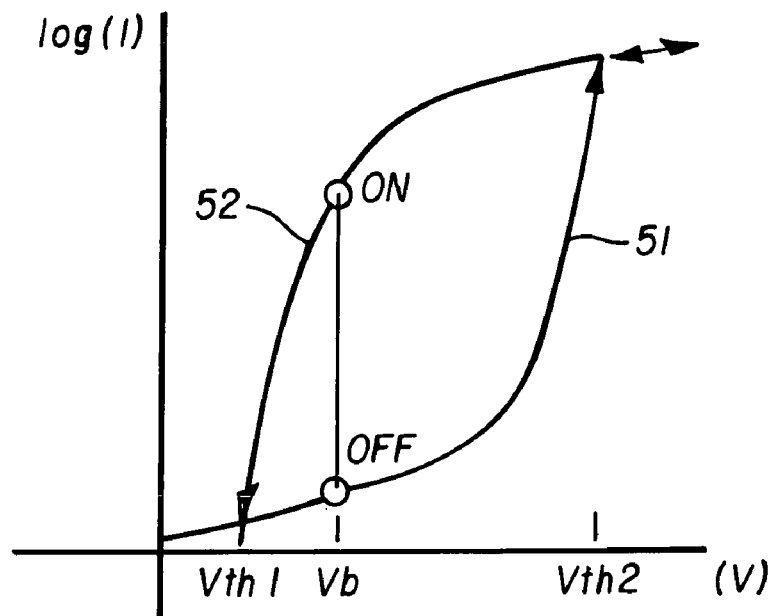
FIG. 19 is a diagram schematically illustrating a voltage-current characteristic of the conventional switching element.
Figure 20:
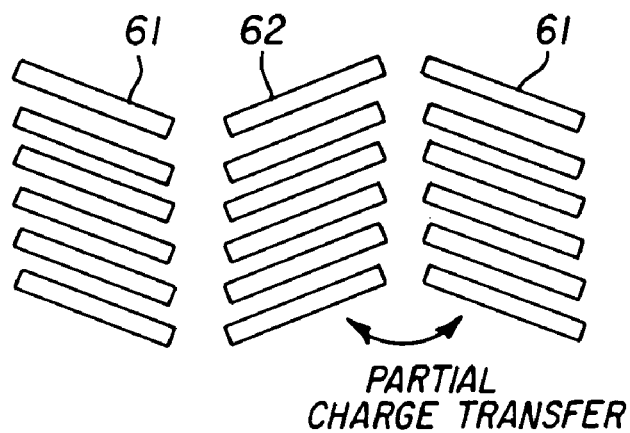
FIG. 20 is a schematic drawing illustrating the structure of an organic bistable material of the conventional two-component system.

A current-voltage characteristic was measured in room temperature environment for each switching element of above-described Working Examples 1 to 3 and the low-transition voltage Vth1 and high-transition voltage Vth2 that are the threshold voltages shown in FIG. 19 were measured. All the results are shown in Table 1. Further, FIGS. 7 to 9 show the current-voltage characteristics relating to respective switching elements.

As for the measurement conditions, an electric resistor of 1 MΩ was connected in series to each switching element, electric current in the ON state was restricted, and damage of the elements caused by overcurrent was inhibited.

TABLE 1

| | Vth1 (V) | Vth2 (V) |
|---|---|---|
| Working Example 1 | 0.6 | 21.2 |
| Working Example 2 | 5.4 | 14.6 |
| Working Example 3 | 0.0 | 5.0 |

As shown in Table 1 and in FIGS. 7 to 9, in the switching elements of Working Examples 1 and 2, the voltage of transition from the OFF state to the ON state is clearly much higher than that of Working Example 3.

Thus, in Working Example 1 illustrated by FIG. 7, at a low-transition voltage Vth1 of 0.6 V or lower, a transition was made from the low-resistance state to the high-resistance state (transition from the ON state to the OFF state) and the resistance value changed. Further, at a high-transition voltage Vth2 of 21.2 V or higher, a transition was made from a high-resistance state to the low-resistance state (transition from the OFF state to the ON state) and the resistance value changed.

In Working Example 2 illustrated by FIG. 8, at a low-transition voltage Vth1 of 5.4 V or lower, a transition was made from the low-resistance state to the high-resistance state (transition from the ON state to the OFF state) and the resistance value changed. Further, at a high-transition voltage Vth2 of 14.6 V or higher, a transition was made from a high-resistance state to the low-resistance state (transition from the OFF state to the ON state) and the resistance value changed.

TEST EXAMPLE 2

Figure 10:
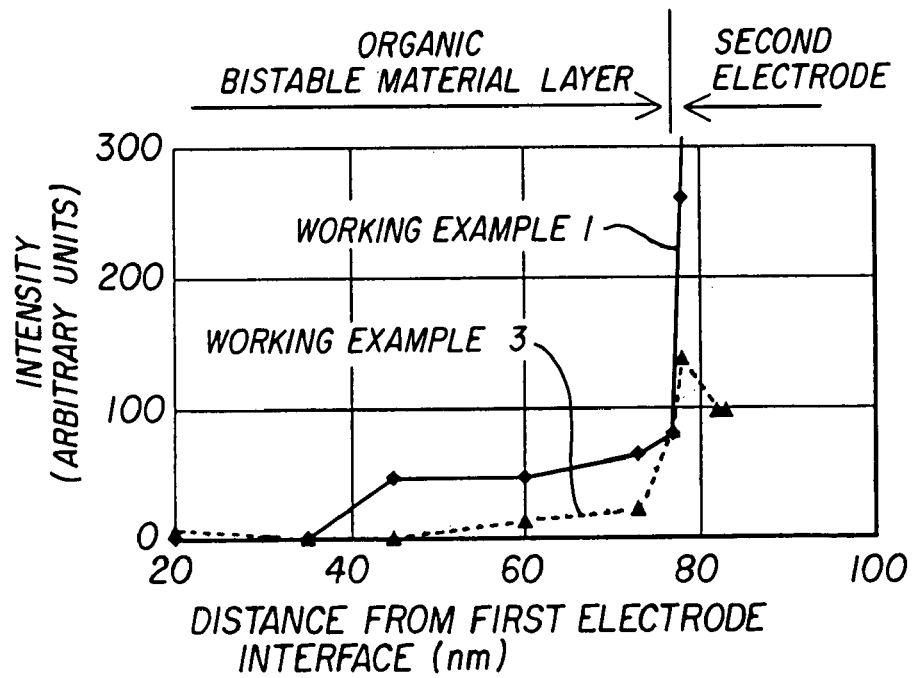
FIG. 10 is a diagram showing the results obtained in metal composition analysis of the cross section by TEM-EPMA in an embodiment.

In order to verify the difference between Working Example 1 and Working Example 3, the composition analysis was conducted by using TEM-EPMA with respect to the diffusion behavior of the gold into the organic bistable material layer 30. The results are shown in FIG. 10. FIG. 10 demonstrates that in Working Example 3 with a substrate temperature during vapor deposition of 20° C., gold did not diffuse into the organic bistable material layer 30. On the other hand, it is clear that in Working Example 1 with a substrate temperature during vapor deposition of 50° C., gold diffused into the organic bistable material layer 30.

WORKING EXAMPLE 4

The switching element with a configuration shown in FIG. 4 was produced by the following procedure.

The switching element of Working Example 4 was formed by using a glass substrate as the substrate 10 and successively forming thin films by vacuum vapor depositing aluminum as the first electrode layer 21*a*, a quinomethane-based compound as the diffusion inhibiting layer 31, a dicyano-based compound as the organic bistable material layer 30, and gold as the second electrode layer 21*b*. The compound with the below-described structural formula (I-1) was used as the quinomethane-based compound and the compound with the below-described structural formula (III) was used as the dicyano-based compound.

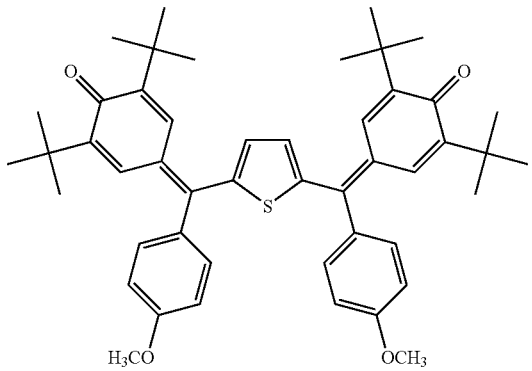

(I-1)

-continued (III)

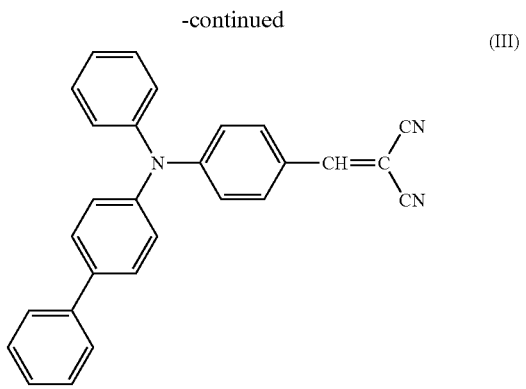

Further, the first electrode layer 21*a*, diffusion inhibiting layer 31, organic bistable material layer 30, and second electrode layer 21*b* were formed to have a thickness of 100 nm, 20 nm, 40 nm, and 100 nm, respectively. The vapor deposition apparatus performed diffusion pump gas discharge to a degree of vacuum of 3×10-6 Torr. Vapor deposition of aluminum, quinomethane-based compound, and dicyano-based compound was conducted at a substrate temperature of 20° C. and a film growth rate of 3 Å/sec, 2 Å/sec, and 2 Å/sec, respectively. Further, gold deposition was conducted by raising the substrate temperature to 35° C. and forming the film at a rate of 3 Å/sec by a resistance heating method. Vapor deposition of each layer was conducted continuously in the same vapor deposition apparatus under conditions preventing contact of samples with the air during vapor deposition.

WORKING EXAMPLE 5

A switching element was obtained under the same conditions as in Working Example 4, except that the diffusion inhibiting layer 31 was not used and the thickness of the quinomethane-based compound represented by the structural formula (I-1) was 80 nm and used as the organic bistable material layer 30.

WORKING EXAMPLE 6

The switching element of Working Example 6 was obtained by using a glass substrate as the substrate 10, successively forming thin films by vacuum vapor depositing gold as the electrode layer 21*a*, a carbonitrile-based compound as the organic bistable material layer 30, a quinomethane-based compound as the diffusion inhibiting layer 31, and gold as the electrode layer 21*b*, using the compound with the below-described structural formula (IV) as the carbonitrile-based compound, using the compound with the below-described structural formula (I-13) as the quinomethane-based compound, and forming the films of the electrode layer 21*a*, bistable material layer 30, diffusion inhibiting layer 31, and electrode layer 21*b* so that they had a thickness of 100 nm, 50 nm, 50 nm, and 100 nm, respectively.

(IV)

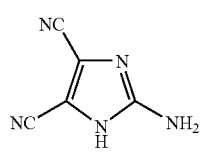

-continued (I-13)

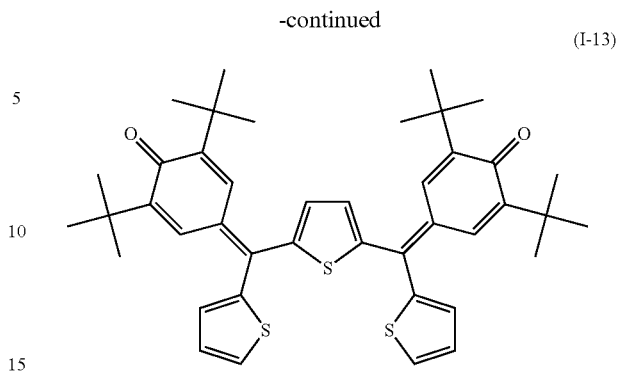

TEST EXAMPLE 3

A current-voltage characteristic was measured in room temperature environment for each switching element of above-described Working Examples 4 to 6. Thus, the voltage was raised from zero to Vth2 at which the transition from the OFF state to the ON state was measured and then lowered to Vth1 at which the transition from the ON state to the OFF state was measured. After the voltages Vth1 and Vth2 were measured, the voltage was again raised to Vth2 at which the transition from the OFF state to the ON state was measured and then returned to zero. The samples were then stored for 10 days at room temperature. As for the measurement conditions, an electric resistor of 1 MΩ was connected in series to each switching element, electric current in the ON state was restricted, and damage of the elements caused by overcurrent was inhibited.

Figure 11:
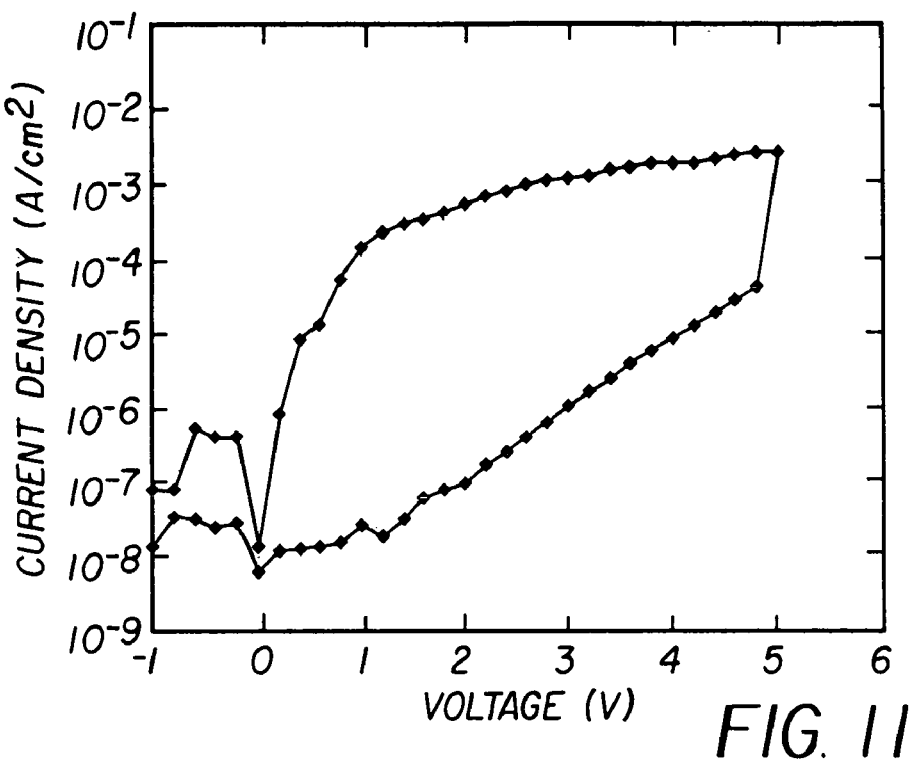
FIG. 11 is a diagram showing a current-voltage characteristic of a switching element in Working Example 4.
Figure 12:
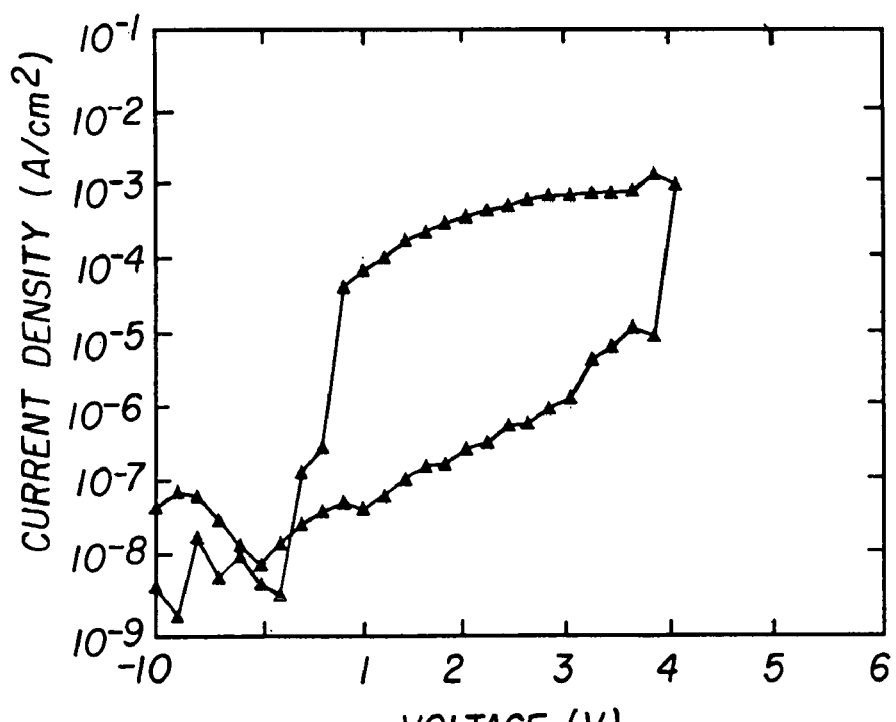
FIG. 12 is a diagram showing a current-voltage characteristic of a switching element in Working Example 5.
Figure 13:
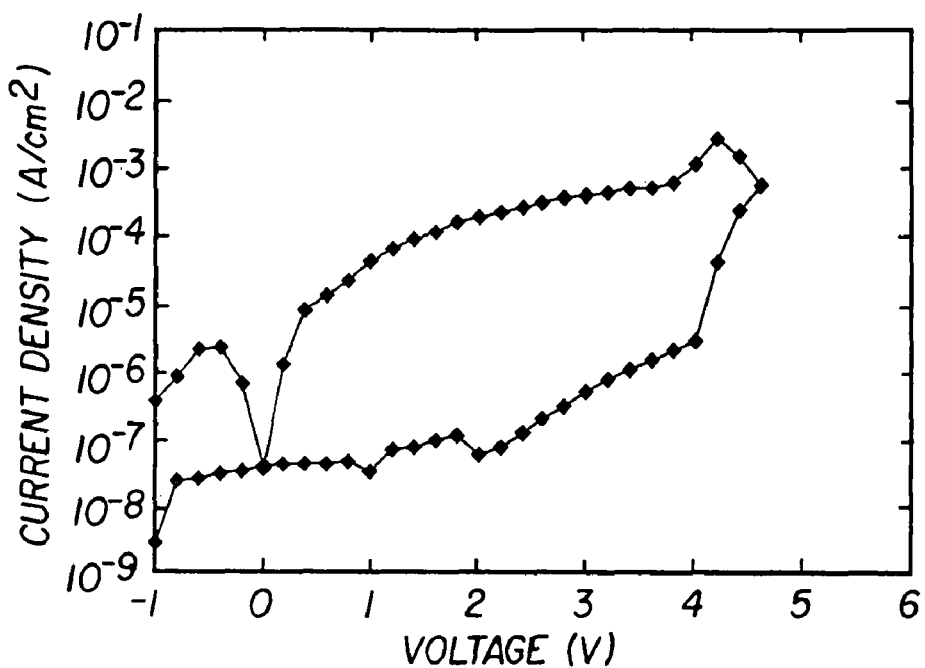
FIG. 13 is a diagram showing a current-voltage characteristic of a switching element in Working Example 6.

FIGS. 11 to 13 show current-voltage characteristics for switching elements of Working Examples 4 to 6, respectively. Table 2 shows measurement results of Vth1, Vth2 in Working Examples 4 to 6. Vth1 assumed a negative value in all the examples.

TABLE 2

|  | Vth1 (V) | Vth2 (V) |
| --- | --- | --- |
| Working Example 4 | −0.8 | 5.0 |
| Working Example 5 | −1.6 | 4.0 |
| Working Example 6 | −¼ | 4.6 |

In the measurements conducted after 10 days, each of 10 measurement points in Working Examples 4 to 6 remembered the final state (ON state) that was assumed prior to 10 days and demonstrated the current—voltage characteristic of the ON state, thereby confirming a memory ability.

Further, Table 2 and FIGS. 11 to 13 show that in Working Examples 4 to 6, good bistable characteristics were obtained: the average low threshold voltage Vth1 was −14 to −0.8 V, the average high threshold voltage Vth2 was 4.0 to 5.0 V, and a value of 1000 or more was obtained as the ratio of the low-resistance state to the high-resistance state.

TEST EXAMPLE 4

Figure 14:
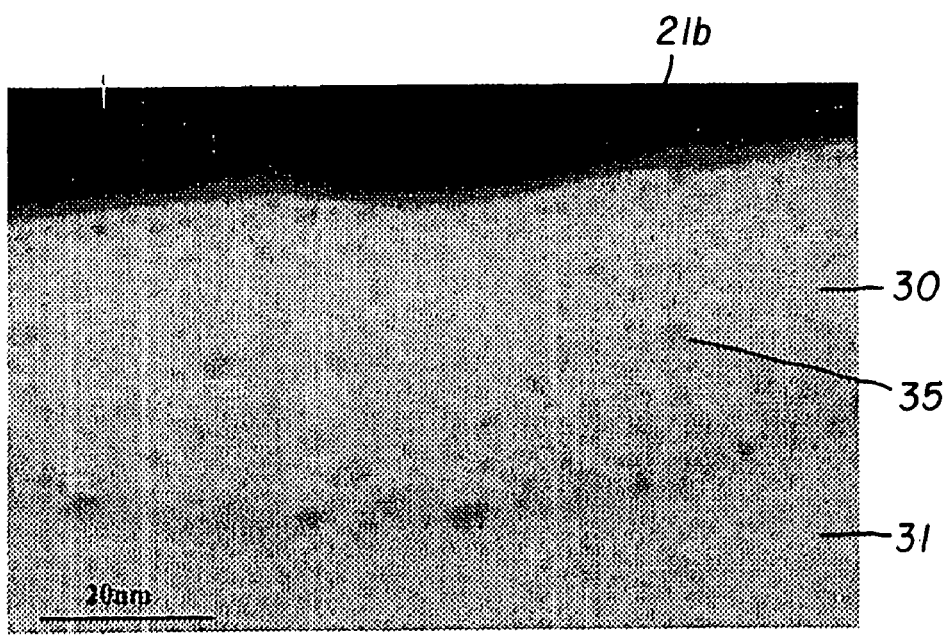
FIG. 14 is cross-sectional microgram obtained by TEM of the switching element of Working Example 4.
Figure 15:
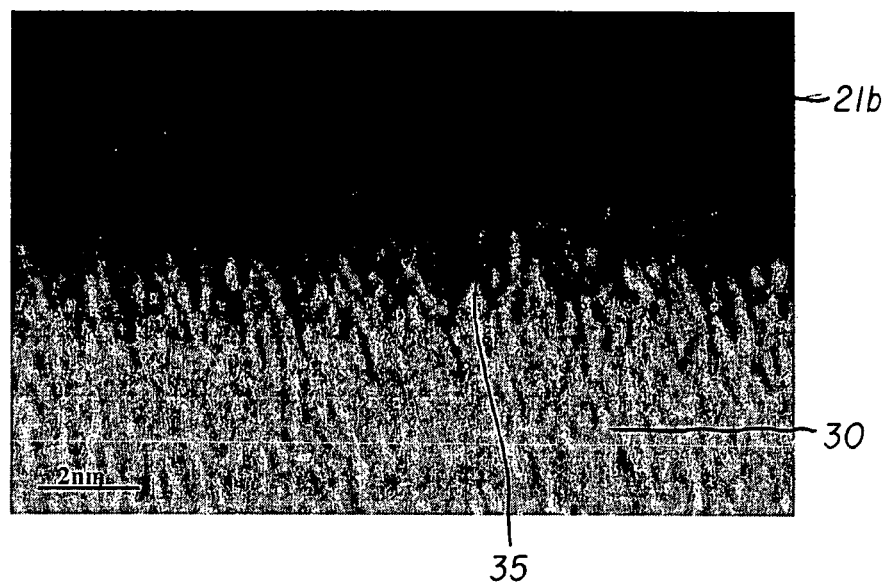
FIG. 15 is cross-sectional microgram obtained by TEM of the switching element of Working Example 5.

FIGS. 14, 15 demonstrate the results obtained by conducting cross-sectional TEM observations (transmission electron microscope) of the interface of the organic bistable material layer 30 and second electrode layer 21*b* in Working Examples 4 and 5, respectively.

FIG. 14 demonstrates that, in Working Example 4, particles 35 of gold with a diameter of about 2 nm diffused to a depth of about 40 nm in the organic bistable material layer 30, but gold did not diffuse into the diffusion inhibiting layer 31 and the diffusion inhibiting layer 31 comprising the quinomethane compound inhibited the diffusion of gold.

Further, FIG. 15 demonstrates that, in Working Example 5, particles 35 of gold present in the organic bistable material layer 30 diffused through the interface to a depth of several nanometers, but did not diffuse into the entire organic bistable material layer 30, and when the quinomethane compound was used as the organic bistable material layer 30, because the diffusion rate of gold was low, the leakage current could be prevented even without providing the diffusion inhibiting layer 31.

WORKING EXAMPLE 7

The switching element with a configuration shown in FIG. 1 was produced by the following procedure.

The switching element was formed by using a glass substrate as the substrate 10 and successively forming thin films by vacuum vapor depositing aluminum as the first electrode layer 21a, a monoquinomethane-based compound as the organic bistable material layer 30, and gold as the second electrode layer 21b. The compound with the below-described structural formula (II-1) was used as the monoquinomethane-based compound.

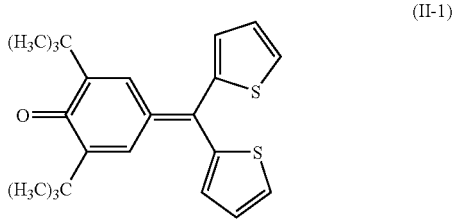

(II-1)

Further, the first electrode layer 21a, organic bistable material layer 30, and second electrode layer 21b were formed to have a thickness of 100 nm, 80 nm, and 100 nm, respectively. The vapor deposition apparatus performed diffusion pump gas discharge to a degree of vacuum was 3×10-6 Torr. Vapor deposition of aluminum was conducted at a film growth rate of 3 Å/sec by a resistance heating method, vapor deposition of the monoquinomethane-based compound was conducted at a film growth rate of 2 Å/sec by a resistance heating method, and vapor deposition of gold was conducted at a film growth rate of 3 Å/sec by a resistance heating method. Vapor deposition of each layer was conducted continuously in the same vapor deposition apparatus under conditions preventing contact of samples with the air during vapor deposition.

WORKING EXAMPLE 8

A switching element was formed by using a glass substrate as the substrate 10 and successively forming thin films by vacuum vapor depositing aluminum as the first electrode layer 21a, a monoquinomethane-based compound as the organic bistable material layer 30, and gold as the second electrode layer 21b. The compound with the below-described structural formula (II-2) was used as the monoquinomethane-based compound.

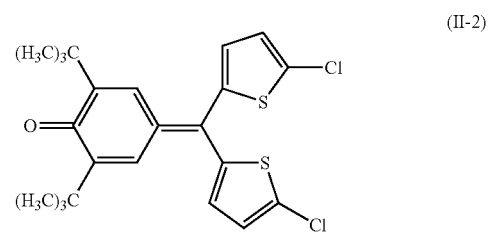

(II-2)

WORKING EXAMPLE 9

A switching element was formed by using a glass substrate as the substrate 10 and successively forming thin films by vacuum vapor depositing aluminum as the first electrode layer 21a, a monoquinomethane-based compound as the organic bistable material layer 30, and gold as the second electrode layer 21b. The compound with the below-described structural formula (II-9) was used as the monoquinomethane-based compound.

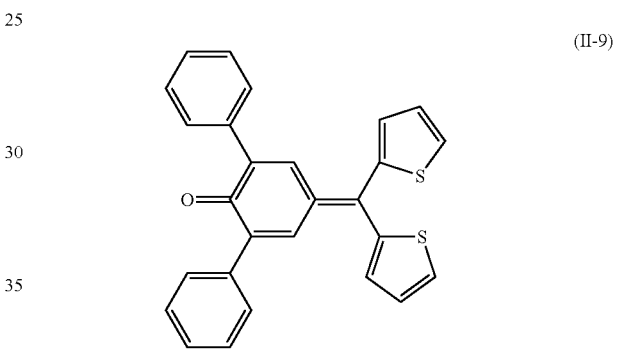

(II-9)

TEST EXAMPLE 5

Figure 16:
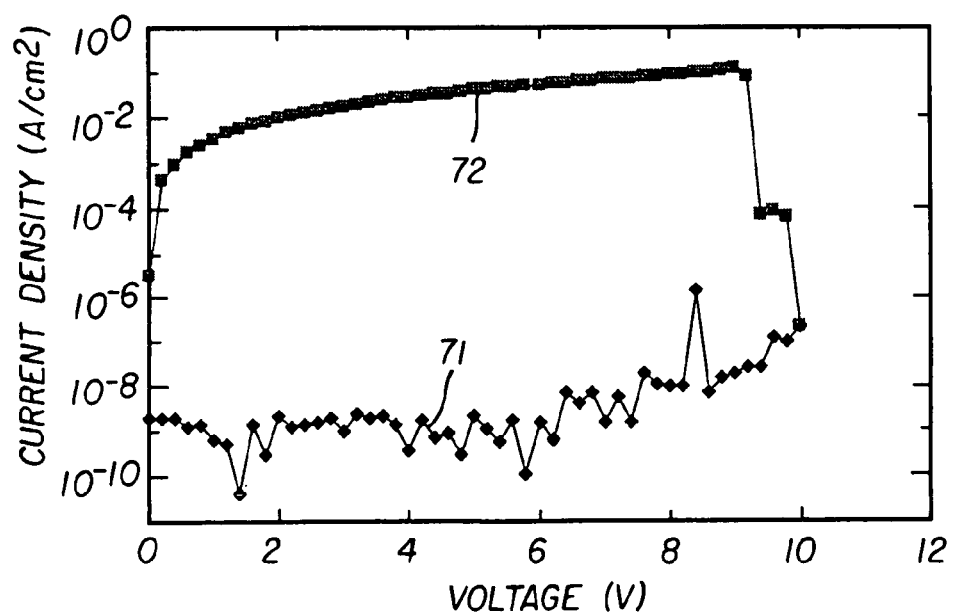
FIG. 16 is a diagram showing a current-voltage characteristic of a switching element in Working Example 7.
Figure 17:
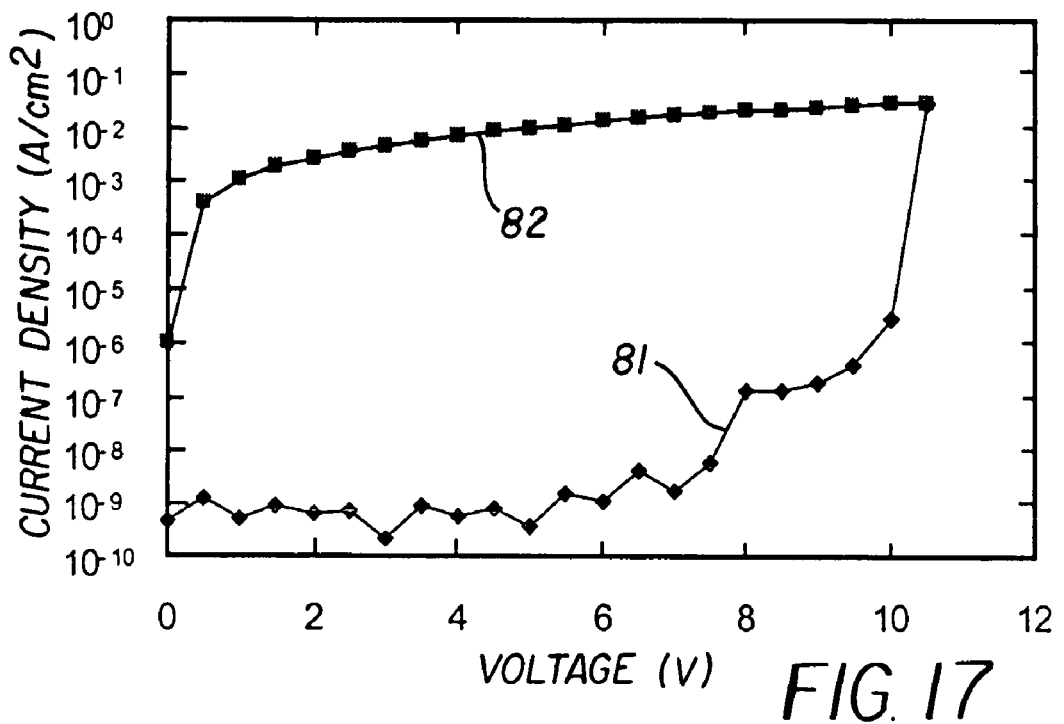
FIG. 17 is a diagram showing a current-voltage characteristic of a switching element in Working Example 8.
Figure 18:
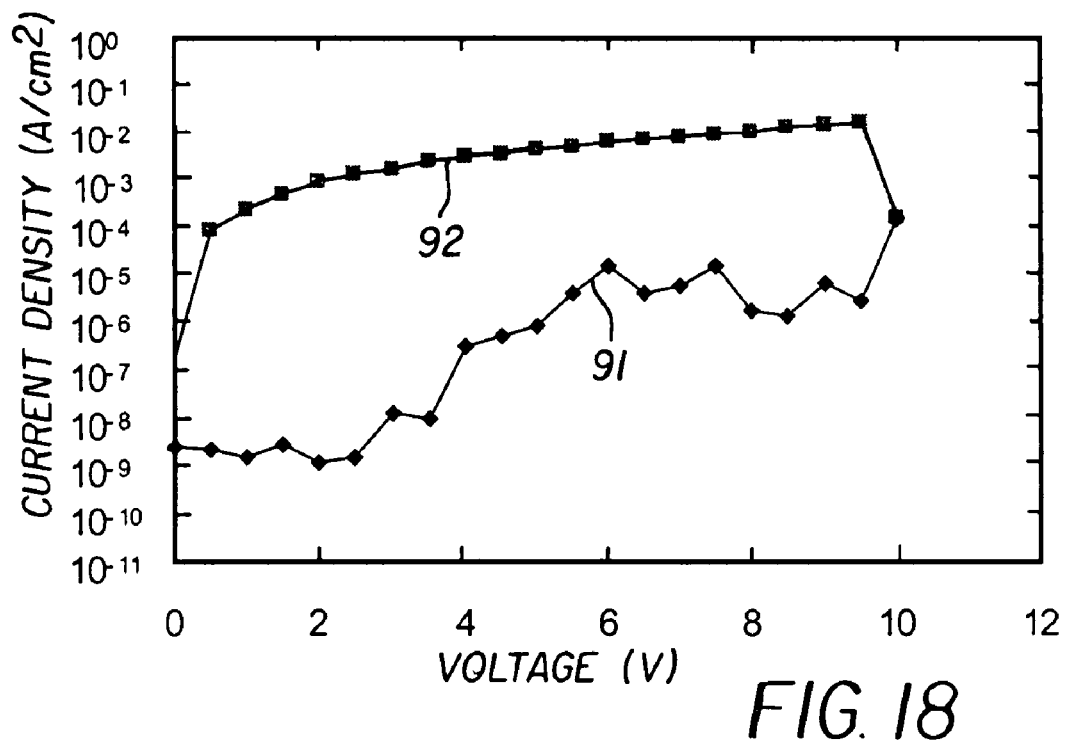
FIG. 18 is a diagram showing a current-voltage characteristic of a switching element in Working Example 9.

A current-voltage characteristic was measured in room temperature environment for each switching element of above-described Working Examples 7 to 9 and the low threshold voltage Vth1 and high threshold voltage Vth2 that are the threshold voltages shown in FIG. 19 were measured. All the results are shown in Table 3. FIGS. 16 to 18 show current-voltage characteristics relating to switching elements of Working Examples 7 to 9.

TABLE 3

|  | Vth1 (V) | Vth2 (V) |
|---|---|---|
| Working Example 7 | 0.0 | 10.0 |
| Working Example 8 | 0.0 | 10.0 |
| Working Example 9 | 0.0 | 9.5 |

The results shown in Table 3 and FIGS. 16 to 18 demonstrate that bistability of high-resistance states 71, 81, 91 and low-resistance states 72, 82, 92 was obtained for switching elements of Working Examples 7 to 9, respectively.

Thus, in Working Example 7 of FIG. 16, at a low threshold voltage Vth1 of 0.0 V, a transition was made from the low-resistance state 72 to the high-resistance state 71 (transition from the ON state to the OFF state) and the resistance value changed. Further, at a high threshold voltage Vth2 of 10.0 V or higher, a transition was made from a high-resistance state 71 to the low-resistance state 72 (transition from the OFF state to the ON state), the resistance value changed, and a value of about 106 was obtained as the ratio of the low-resistance state to the high-resistance state at this time.

In Working Example 8 of FIG. 17, at a low threshold voltage Vth1 of 0.0 V, a transition was made from the low-resistance state 82 to the high-resistance state 81 (transition from the ON state to the OFF state) and the resistance value changed. Further, at a high threshold voltage Vth2 of 10.0 V or higher, a transition was made from a high-resistance state 81 to the low-resistance state 82 (transition from the OFF state to the ON state), the resistance value changed, and a value of about 104 was obtained as the ratio of the low-resistance state to the high-resistance state at this time.

In Working Example 9 of FIG. 18, at a low threshold voltage Vth1 of 0.0 V, a transition was made from the low-resistance state 92 to the high-resistance state 91 (transition from the ON state to the OFF state) and the resistance value changed. Further, at a high threshold voltage Vth2 of 9.5 V or higher, a transition was made from a high-resistance state 91 to the low-resistance state 92 (transition from the OFF state to the ON state), the resistance value changed, and a value of about 103 was obtained as the ratio of the low-resistance state to the high-resistance state at this time.

Thus, bistability was obtained in all the switching elements of Working Examples 7 to 9, and a bistable state with a low threshold voltage Vth1 of 0.0 V and a high threshold voltage Vth2 of 9.5-10.0 V shown in Table 2 was obtained.

INDUSTRIAL APPLICABILITY

In the switching element in accordance with the present invention, fluctuations of material composition can be inhibited and a uniform bistable characteristic can be obtained. This switching element is suitable for mass production, has a high transition voltage and demonstrates excellent cyclic performance. Therefore, it can be advantageously used for as a switching element for driving an organic EL display panel or for a high-density memory.

The invention claimed is:

1. A switching element having two stable resistance values with respect to the voltage applied between electrodes, comprising:
   a substrate,
   a first electrode layer,
   an organic bistable material layer, and
   a second electrode layer, said first electrode layer, said organic bistable material layer and said second electrode being successively formed as thin films on said substrate
   wherein the organic bistable material constituting said organic bistable material layer is a quinomethane-based compound represented by the general formula (I) below:

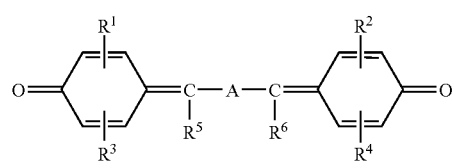

(I)

wherein each of $R^1$-$R^4$ represents a group selected from a hydrogen atom, an optionally substituted $C_{1-6}$ alkyl group, and an optionally substituted aryl group, where $R^1$-$R^4$ may be same or different, each of $R^5$ and $R^6$ represents an optionally substituted aryl group or an optionally substituted hetero ring, where $R^5$, $R^6$ may be same or different and A represents a group selected from groups (1)-(10) shown below

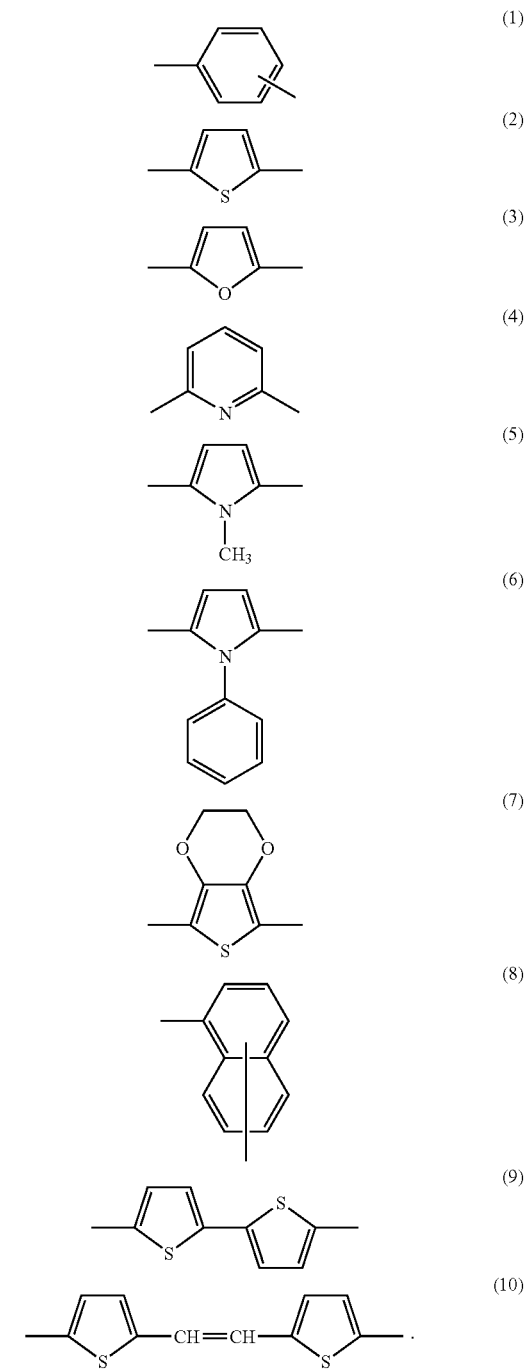

2. The switching element of claim 1, wherein said second electrode layer is formed by vapor deposition and the temperature of said substrate during said vapor deposition is 30-150° C.

3. The switching element of claim 1, wherein said second electrode layer comprises at least one species selected from gold, platinum, rhodium, silver, and chromium.

* * * * *